US010039525B2

(12) United States Patent
Yoshiara et al.

(10) Patent No.: US 10,039,525 B2
(45) Date of Patent: Aug. 7, 2018

(54) ULTRASOUND DIAGNOSTIC APPARATUS AND IMAGE PROCESSING METHOD

(71) Applicant: Toshiba Medical Systems Corporation, Otawara-shi (JP)

(72) Inventors: Hiroki Yoshiara, Nasushiobara (JP); Yuko Kanayama, Nasushiobara (JP); Yoshitaka Mine, Nasushiobara (JP); Cong Yao, Otawara (JP); Go Tanaka, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 538 days.

(21) Appl. No.: 14/713,720

(22) Filed: May 15, 2015

(65) Prior Publication Data

US 2015/0245819 A1 Sep. 3, 2015

Related U.S. Application Data

(63) Continuation of application No. PCT/JP2013/081063, filed on Nov. 18, 2013.

(30) Foreign Application Priority Data

Nov. 16, 2012 (JP) ................................ 2012-252524
Nov. 18, 2013 (JP) ................................ 2013-238159

(51) Int. Cl.
*A61B 8/08* (2006.01)
*A61B 8/06* (2006.01)
(Continued)

(52) U.S. Cl.
CPC .............. *A61B 8/5207* (2013.01); *A61B 8/06* (2013.01); *A61B 8/0841* (2013.01);
(Continued)

(58) Field of Classification Search
CPC ...................................................... A61B 8/481
See application file for complete search history.

(56) References Cited

U.S. PATENT DOCUMENTS

| 2003/0208123 | A1* | 11/2003 | Panescu | ................. | A61B 8/481 |
| | | | | | 600/431 |
| 2005/0187475 | A1* | 8/2005 | Nakaya | .................... | A61B 8/06 |
| | | | | | 600/439 |

(Continued)

FOREIGN PATENT DOCUMENTS

| CN | 101511295 A | 8/2009 |
| CN | 102238921 A | 11/2011 |

(Continued)

OTHER PUBLICATIONS

International Written Opinion dated Dec. 17, 2013 for PCT/JP2013/081063 filed Nov. 18, 2013.*

(Continued)

*Primary Examiner* — Tse Chen
*Assistant Examiner* — Nate S Sunwoo
(74) *Attorney, Agent, or Firm* — Oblon, McClelland, Maier & Neustadt, L.L.P.

(57) ABSTRACT

An ultrasound diagnostic apparatus according to an embodiment includes processing circuitry. The processing circuitry is configured to obtain the position of the boundary of a region of interest that is set in first ultrasound image data of a subject. The processing circuitry is configured to generate second ultrasound image data by assigning a pixel value to each of pixels of which a change of the brightness value between before and after a contrast enhancement is equal to or larger than a threshold value with regard to pre-contrast-enhanced image data and post-contrast-enhanced image data of the subject both of which were acquired after a treatment using a puncture needle has been performed, the assigned pixel value corresponding to the distance between the pixel (Continued)

and the boundary of the region of interest. The processing circuitry is configured to cause a display unit to display the second ultrasound image data.

19 Claims, 14 Drawing Sheets

(51) Int. Cl.
*A61B 8/00* (2006.01)
*A61B 17/34* (2006.01)
*A61B 34/20* (2016.01)
*A61B 90/00* (2016.01)
*A61B 18/14* (2006.01)
*A61B 18/00* (2006.01)

(52) U.S. Cl.
CPC .......... *A61B 8/0866* (2013.01); *A61B 8/0883* (2013.01); *A61B 8/463* (2013.01); *A61B 8/466* (2013.01); *A61B 8/469* (2013.01); *A61B 8/481* (2013.01); *A61B 8/483* (2013.01); *A61B 8/523* (2013.01); *A61B 17/3403* (2013.01); *A61B 34/20* (2016.02); *A61B 90/37* (2016.02); *A61B 2017/3413* (2013.01); *A61B 2018/00738* (2013.01); *A61B 2018/1425* (2013.01); *A61B 2034/2051* (2016.02); *A61B 2090/378* (2016.02); *A61B 2560/0475* (2013.01)

(56) References Cited

U.S. PATENT DOCUMENTS

| | | | | |
|---|---|---|---|---|
| 2011/0160717 A1* | 6/2011 | van der Weide | ...... | A61B 18/18 606/33 |
| 2011/0251607 A1* | 10/2011 | Kruecker | ........... | A61B 18/1206 606/34 |
| 2014/0270377 A1* | 9/2014 | Kanda | ................ | A61B 1/00009 382/103 |
| 2015/0250437 A1* | 9/2015 | Zaiki | .................... | A61M 5/007 600/301 |
| 2015/0332455 A1* | 11/2015 | Kobayashi | ............. | A61B 6/481 382/131 |

FOREIGN PATENT DOCUMENTS

| | | | |
|---|---|---|---|
| JP | 2007-117384 A | 5/2007 |
| JP | 2009-279079 A | 12/2009 |
| JP | 2010-099193 A | 5/2010 |
| JP | 2010-274043 A | 12/2010 |
| JP | 2011-200533 A | 10/2011 |
| JP | 2012-045198 A | 3/2012 |
| WO | WO 2008/008545 A2 | 1/2008 |
| WO | WO 2012/147733 A1 | 11/2012 |

OTHER PUBLICATIONS

Office Action dated May 29, 2015 for CN201380002850 with machine and human translation into English.*
Second Office Action dated Jan. 4, 2016 for CN201380002850 with machine and human translation into English.*
International Search Report dated Dec. 17, 2013 for PCT/JP2013/081063 filed Nov. 18, 2013 with English Translation.
Combined Office Action and Search Report dated May 29, 2015 in Chinese Patent Application No. 201380002850.9 (with English Translation of Category of Cited Documents).

* cited by examiner

FIG.4
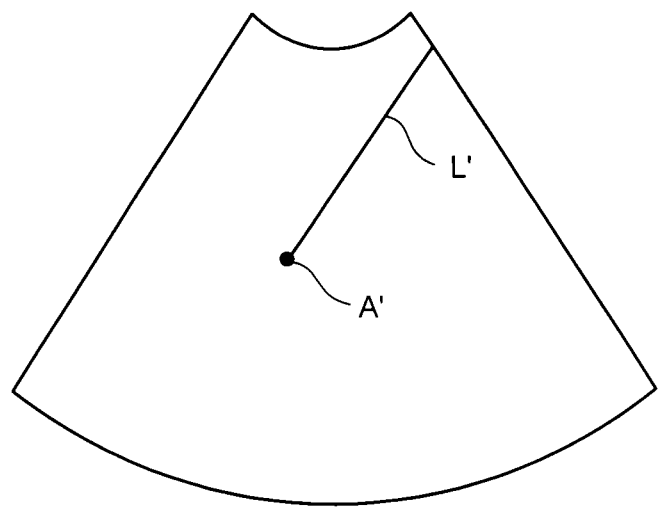
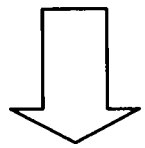
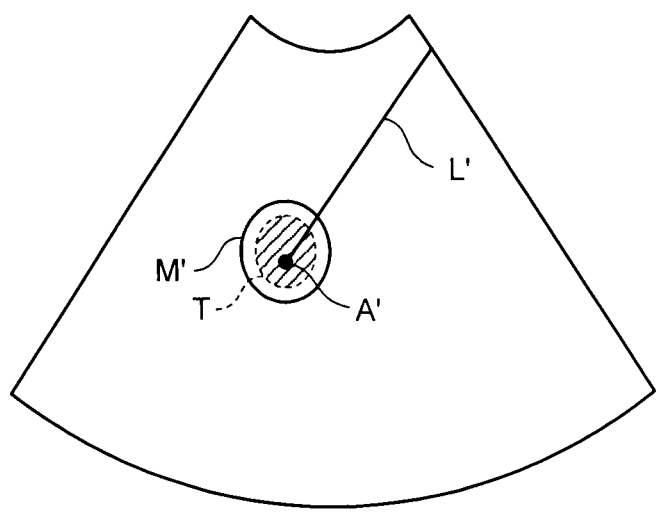

ULTRASOUND DIAGNOSTIC APPARATUS AND IMAGE PROCESSING METHOD

CROSS-REFERENCE TO RELATED APPLICATIONS

This application is a continuation of PCT international application Ser. No. PCT/JP2013/081063 filed on Nov. 18, 2013 which designates the United States, incorporated herein by reference, and which claims the benefit of priority from Japanese Patent Application No. 2012-252524, filed on Nov. 16, 2012, and Japanese Patent Application No. 2013-238159, filed on Nov. 18, 2013, the entire contents of which are incorporated herein by reference.

FIELD

Embodiments described herein relate generally to an ultrasound diagnostic apparatus and an image processing method.

BACKGROUND

Ultrasound diagnostic apparatus plays an important role in today's medicine as a medical image diagnostic apparatus having various advantages such as convenient operability, non-invasive nature without the possibility of radiation exposure, and compactness of the scale of the system. Specifically, ultrasound diagnostic apparatuses are capable of displaying, in a real-time manner, the state of movements of an examined target (e.g., heartbeats, movements of a fetus) by a convenient operation such as pressing an ultrasound probe against the body surface of an examined subject. Further, because ultrasound diagnostic apparatuses have a high level of safety due to the non-invasive nature, it is possible to repeatedly perform medical examinations. Further, compared to other types of medical image diagnostic apparatuses such as X-ray diagnostic apparatuses, X-ray Computed Tomography (CT) apparatuses, and Magnetic Resonance Imaging (MRI) apparatuses, the scale of a system using an ultrasound diagnostic apparatus is smaller, which makes it possible to easily perform a medical examination even at bedside. Further, some ultrasound diagnostic apparatuses have been developed to be so compact as to be carried in one hand. Such ultrasound diagnostic apparatuses can be easily used in medical sites including obstetrics departments and home medical care.

Further, in recent years, intravenously-administered ultrasound contrast agents have been available as products, so that "contrast echo methods" can be implemented. In the following sections, ultrasound contrast agents may simply be referred to as "contrast agents". For example, one of the purposes of a contrast echo method is, when performing a medical examination on the heart or the liver, to inject a contrast agent through a vein so as to enhance bloodstream signals and to evaluate bloodstream dynamics. In many contrast agents, microbubbles function as reflection sources. For example, a second-generation ultrasound contrast agent called "Sonazoid (registered trademark)" that was recently launched in Japan includes microbubbles configured with phospholipid enclosing fluorocarbon (perfluorobutane) gas therein. When implementing the contrast echo method, it is possible to stably observe a reflux of the contrast agent, by using a transmission ultrasound wave having a medium-low sound pressure at such a level that does not destroy the microbubbles.

Further, various applied usages have been developed in the field of treatments using ultrasound diagnostic apparatuses. For example, in some situations, a needle biopsy to perform a pathological examination on a tumor tissue may be performed by a guide of ultrasound waves while using an ultrasound diagnostic apparatus. Further, a puncture process using a Radiofrequency Ablation (RFA) needle (an electrode needle) to perform an RFA process on a local tumor such as hepatic cancer is performed by a guide of ultrasound waves. In addition, ultrasound diagnostic apparatuses are also used for judging effects of RFA treatments.

An RFA treatment is performed by inserting an electrode needle through the body surface toward a lesion site (a tumor part) so as to induce coagulation necrosis in the lesion site with high temperature generated by radiofrequency. In recent years, the contrast enhanced ultrasound waves described above are often used for judging the effects of RFA treatments. Specifically, to judge the effect of an RFA treatment, it is checked to see whether the bloodstream feeding the tumor (tumor bloodstream) has disappeared in the treatment site where the RFA treatment was performed, by implementing a contrast echo method. As for the region (a treatment plan region) on which an RFA treatment is to be performed, it is important to securely arrange a margin of approximately 5 mm in all directions around the boundary of a tumor for the purpose of preventing a recurrence of the tumor. During an RFA treatment, however, the image of the tissue may change, and gas may be generated, due to the ablation. For this reason, even when viewing contrast enhanced images taken after a treatment, it is difficult for doctors to judge the effect of the treatment, because the position of the needle tip and the position of the boundary of the tumor are difficult to determine. Further, in some situations, performing an RFA treatment only once may be insufficient depending on the size and the shape of the tumor and due to the cooling effect of blood vessels near the tumor. Thus, to perform an additional treatment, it is necessary to accurately understand the bloodstream remaining sites on the inside of the treatment plan region and in a nearby region on the outside of the treatment plan region.

In other words, to judge the effect of an RFA treatment, it is necessary to understand whether there is an inflow of contrast agent to the treatment plan region securely and conveniently. However, the usual process of judging the effect of an RFA treatment is subjectively performed by a doctor. For this reason, a method for judging the effect of a treatment objectively is known by which a position aligning process is performed on post-treatment ultrasound volume data and pre-treatment reference image represented by X-ray CT volume data, MRI volume data, or ultrasound volume data. According to this method, the quantitative effect of a treatment is presented to the doctor, by measuring the distance between the boundary of a tumor and the boundary of an ablated region and displaying the measured distance in color, based on the position alignment performed on the pre-treatment reference image and the post-treatment ultrasound volume data.

However, it is difficult to retrieve the pieces of volume data from storage and to perform the position aligning process on the two pieces of volume data, in a short period of time during a puncture treatment. For example, as explained above, the position aligning process can be difficult in some situations because the image of the tissue may change between before and after a treatment and because gas may be generated. In addition, in the actual sites of treatments, doctors have to instantly determine whether there is a need for an additional treatment.

BRIEF DESCRIPTION OF THE DRAWINGS

FIG. 4 and FIG. 5 are drawings for explaining the obtaining unit illustrated in FIG. 1;

DETAILED DESCRIPTION

An ultrasound diagnostic apparatus according to an embodiment includes processing circuitry. The processing circuitry is configured to obtain the position of the boundary of a region of interest that is set in first ultrasound image data of a subject. The processing circuitry is configured to generate second ultrasound image data by assigning a pixel value to each of pixels of which a change of the brightness value between before and after a contrast enhancement is equal to or larger than a threshold value with regard to pre-contrast-enhanced image data and post-contrast-enhanced image data of the subject both of which were acquired after a treatment using a puncture needle has been performed, the assigned pixel value corresponding to the distance between the pixel and the boundary of the region of interest. The processing circuitry is configured to cause a display to display the second ultrasound image data.

Exemplary embodiments of an ultrasound diagnostic apparatus will be explained in detail below, with reference to the accompanying drawings.

First Embodiment

Figure 1:
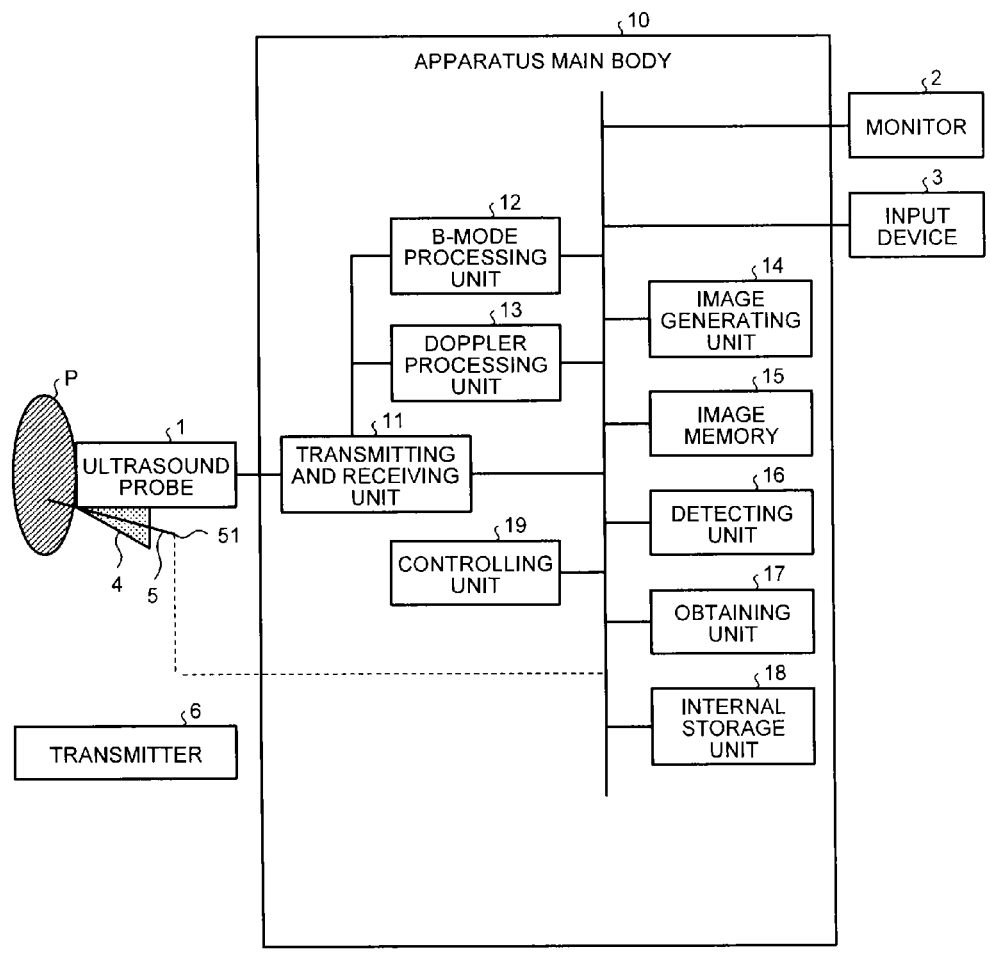
FIG. 1 is a diagram of an exemplary configuration of an ultrasound diagnostic apparatus according to a first embodiment.

First, a configuration of an ultrasound diagnostic apparatus according to a first embodiment will be explained. FIG. 1 is a diagram of an exemplary configuration of the ultrasound diagnostic apparatus according to the first embodiment. As illustrated in FIG. 1, the ultrasound diagnostic apparatus according to the first embodiment includes an ultrasound probe 1, a monitor 2, an input device 3, and an apparatus main body 10.

The ultrasound probe 1 is detachably connected to the apparatus main body 10. For example, the ultrasound probe 1 includes a plurality of piezoelectric transducer elements, which generate an ultrasound wave based on a drive signal supplied from a transmitting and receiving unit 11 included in the apparatus main body 10 (explained later). Further, the ultrasound probe 1 receives a reflected wave from an examined subject (hereinafter, a "subject") P and to convert the received reflected wave into an electric signal. Further, the ultrasound probe 1 includes a matching layer that is abutted on the piezoelectric transducer elements, as well as a backing member that prevents backward propagation of ultrasound waves from the piezoelectric transducer elements.

When an ultrasound wave is transmitted from the ultrasound probe 1 to the subject P, the transmitted ultrasound wave is repeatedly reflected on discontinuous surfaces of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the discontinuous surfaces on which the ultrasound wave is reflected. When the transmitted ultrasound pulse is reflected on the surface of a flowing bloodstream, a cardiac wall, and the like, the reflected-wave signal is, due to the Doppler effect, subject to a frequency shift, depending on a velocity component of the moving members with respect to the ultrasound wave transmission direction.

For example, the apparatus main body 10 may be connected to a one-dimensional (1D) array probe which is served as the ultrasound probe 1 for a two-dimensional scan and in which the plurality of piezoelectric transducer elements are arranged in a row. Alternatively, for example, the apparatus main body 10 may be connected to a mechanical four-dimensional (4D) probe or a two-dimensional (2D) array probe which is served as the ultrasound probe 1 for a three-dimensional scan. The mechanical 4D probe is able to perform a two-dimensional scan by employing a plurality of piezoelectric transducer elements arranged in a row like in the 1D array probe and is also able to perform the three-dimensional scan by causing the plurality of piezoelectric transducer elements to swing at a predetermined angle (a swinging angle). The 2D array probe is able to perform the three-dimensional scan by employing a plurality of piezoelectric transducer elements arranged in a matrix formation and is also able to perform a two-dimensional scan by transmitting ultrasound waves in a focused manner.

The first embodiment is applicable to a situation where the ultrasound probe 1 performs a two-dimensional scan on the subject P and to a situation where the ultrasound probe 1 performs a three-dimensional scan on the subject P. In the following sections, an example in which the ultrasound probe 1 performs a three-dimensional scan on the subject P will be explained.

Further, in the first embodiment, a puncture adaptor 4 is attached to the ultrasound probe 1, as illustrated in FIG. 1, to perform a Radiofrequency Ablation (RFA) treatment. Further, a puncture needle 5, which is an electrode needle generating radiofrequency, is attached to the puncture adaptor 4. A doctor inserts the puncture needle 5 attached to the puncture adaptor 4 up to a treatment site of the subject P, while viewing ultrasound image data displayed on the monitor 2 as a result of ultrasound transmissions/receptions performed by the ultrasound probe 1.

It should be noted, however, that the first embodiment is also applicable to a situation where a puncture process using the puncture needle 5 is performed by hand without using the puncture adaptor 4.

Further, although not illustrated in FIG. 1, the puncture needle 5 is connected to a treatment apparatus that controls the output of radiofrequency generated by the puncture needle 5. The treatment apparatus is capable of monitoring the temperature of the puncture needle 5, the output of radiofrequency, and the impedance in an ablated region. The doctor thus performs the RFA treatment using the puncture needle 5, by operating the treatment apparatus.

Further, the puncture needle 5 according to the first embodiment includes a position sensor 51. As illustrated in FIG. 1, for example, the position sensor 51 is installed on the base (e.g., a bracket section) of the puncture needle 5. Alternatively, the position sensor 51 may be installed on a tip section of the puncture needle 5. The position sensor 51 is a magnetic sensor. Further, a transmitter 6 illustrated in FIG. 1 is a device that is installed in an arbitrary position and outwardly forms a magnetic field centered thereon. In the first embodiment, the transmitter 6 is installed near the apparatus main body 10. The first embodiment is also applicable to another situation where the transmitter 6 is attached to the apparatus main body 10. The position sensor 51 detects the three-dimensional magnetic field formed by the transmitter 6. Subsequently, the position sensor 51 transmits information about the detected magnetic field to the apparatus main body 10. For example, the position sensor 51 may transmit the information about the detected magnetic field to the apparatus main body 10 by a wireless communication or a wired communication. In this situation, the position sensor 51 installed on the base of the puncture needle 5 has a length along the direction from the base to the tip end of the puncture needle 5. Thus, the information about the magnetic field detected by the position sensor 51 makes it possible to detect the position of the base of the puncture needle 5 and a three-dimensional orientation of the puncture needle 5. Accordingly, if the insertion path of the puncture needle 5 is assumed to be a straight line and if the length of the puncture needle 5 is known, the information about the magnetic field detected by the position sensor 51 makes it possible to detect the position of the needle tip of the puncture needle 5.

The input device 3 includes a mouse, a keyboard, a button, a panel switch, a touch command screen, a foot switch, a trackball, and the like. The input device 3 receives various types of setting requests from an operator of the ultrasound diagnostic apparatus and transfers the received various types of setting requests to the apparatus main body 10. For example, the input device 3 receives a setting of a region in which an RFA treatment is to be performed, from the operator.

The monitor 2 displays a Graphical User Interface (GUI) used by the operator of the ultrasound diagnostic apparatus to input the various types of setting requests through the input device 3 and an ultrasound image generated by the apparatus main body 10.

The apparatus main body 10 is an apparatus that generates ultrasound image data based on the reflected wave received by the ultrasound probe 1 and includes, as illustrated in FIG. 1, the transmitting and receiving unit 11, a B-mode processing unit 12, a Doppler processing unit 13, an image generating unit 14, an image memory 15, a detecting unit 16, an obtaining unit 17, an internal storage unit 18, and a controlling unit 19.

The transmitting and receiving unit 11 includes a trigger generating circuit, a delaying circuit, a pulser circuit, and the like and supplies the drive signal to the ultrasound probe 1. The pulser circuit repeatedly generates a rate pulse for forming a transmission ultrasound wave at a predetermined rate frequency. Further, the delaying circuit applies a delay period that is required to focus the ultrasound wave generated by the ultrasound probe 1 into the form of a beam and to determine transmission directionality and that corresponds to each of the piezoelectric transducer elements, to each of the rate pulses generated by the pulser circuit.

Further, the trigger generating circuit applies a drive signal (a drive pulse) to the ultrasound probe 1 with timing based on the rate pulses. In other words, the delaying circuit arbitrarily adjusts the transmission directions from the piezoelectric transducer elements surface, by varying the delay periods applied to the rate pulses.

After the drive pulses have reached the piezoelectric transducer elements included in the ultrasound probe 1 from the pulser circuit through a cable, the drive pulses are converted from the electric signals into mechanical vibrations by the piezoelectric transducer elements. The mechanical vibrations are transmitted to a subject's body as ultrasound waves. In this situation, the ultrasound waves, which have mutually-different transmission delay periods depending on the piezoelectric transducer elements, are focused and propagates in predetermined directions. In other words, by varying the transmission delay periods applied to the rate pulses, the delaying circuit arbitrarily adjusts the transmission directions from the piezoelectric transducer elements surface.

The transmitting and receiving unit 11 has a function to be able to instantly change the transmission frequency, the transmission drive voltage, and the like, for the purpose of executing a predetermined scanning sequence based on an instruction from the controlling unit 19 (explained later). In particular, the configuration to change the transmission drive voltage is realized by using a linear-amplifier-type transmitting circuit of which the value can be instantly switched or by using a mechanism configured to electrically switch among a plurality of power source units.

The transmitting and receiving unit 11 includes an amplifier circuit, an Analog/Digital (A/D) converter, an adder, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and further applies reception delay periods required to determine reception directionality to the result of the A/D conversion. On the basis of the applied delay periods, the adder performs an adding process on the reflected-wave signals so as to generate the reflected-wave data. As a result of the adding process performed by the adder, reflected components from the direction corresponding to the reception directionality of the reflected-wave signals are emphasized.

In the manner described above, the transmitting and receiving unit 11 controls the transmission directionality and the reception directionality of the ultrasound transmission/reception. A comprehensive beam used in an ultrasound transmission/reception is thus formed according to the reception directionality and the transmission directionality controlled by the transmitting and receiving unit 11. In this situation, when a two-dimensional scan is performed on the subject P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. When a three-dimensional scan is performed on the subject P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1. Output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data.

The Doppler processing unit 13 receives the reflected-wave data from the transmitting and receiving unit 11, obtains velocity information from the received reflected-wave data by performing a frequency analysis, extracts bloodstream, tissues, and contrast-agent echo components by the Doppler effect, and to further generate data (Doppler data) obtained by extracting moving member information such as an average velocity, a dispersion, a power, and the like, for a plurality of points. The data generated by the B-mode processing unit 12 or the Doppler processing unit 13 may be referred to as raw data.

The B-mode processing unit 12 is capable of changing the frequency band to be imaged by changing a detection frequency by a filtering process. By using this function of the B-mode processing unit 12, the ultrasound diagnostic apparatus according to the first embodiment is capable of performing a Contrast Harmonic Imaging (CHI) process. In other words, from the reflected-wave data of the subject P into whom a contrast agent has been injected, the B-mode processing unit 12 is able to separate, by performing the filtering process, reflected wave data (harmonic data or subharmonic data) of which the reflection source is the contrast agent (microbubbles, bubbles) and reflected-wave data (fundamental harmonic data) of which the reflection source is tissues in the subject P. For example, from the reflected-wave data of the subject P into whom the contrast agent has been injected, the B-mode processing unit 12 is able to generate B-mode data used for generating contrast enhanced image data that uses second harmonic data or to generate B-mode data used for generating tissue image data that uses fundamental harmonic data.

Further, by using the filtering process function of the B-mode processing unit 12 described above, it is possible to generate B-mode data used for generating tissue image data from which noise components are eliminated, by separating the harmonic data or the subharmonic data from the reflected-wave data of the subject P, during a Tissue Harmonic Imaging (THI) process. When performing a harmonic imaging process such as CHI or THI, the B-mode processing unit 12 is able to extract harmonic components by using a method different from the method described above that uses the filtering process. During the harmonic imaging process, it is possible to implement any of the imaging methods including an Amplitude Modulation (AM) method, a Phase Modulation (PM) method, and an AMPM method combining the AM method with the PM method. According to the AM method, the PM method, or the AMPM method, a plurality of ultrasound transmission is performed with respect to the same scanning line, while varying the amplitude and/or the phase. As a result, the transmitting and receiving unit 11 generates and outputs a plurality of pieces of reflected-wave data (reception signals) for each of the scanning lines. After that, the B-mode processing unit 12 extracts the harmonic components by performing an addition/subtraction process depending on the modulation method on the plurality of pieces of reflected-wave data (the reception signals) for each of the scanning lines. After that, the B-mode processing unit 12 generates B-mode data by performing an envelope detection process or the like on the reflected-wave data (the reception signals) of the harmonic components.

For example, when implementing the PM method, the transmitting and receiving unit 11 causes ultrasound waves having mutually the same amplitude and inverted phase polarities (e.g., (−1, 1)) to be transmitted twice for each of the scanning lines, according to a scan sequence set by the controlling unit 19. After that, the transmitting and receiving unit 11 generates a reception signal from the "−1" transmission and a reception signal from the "1" transmission. The B-mode processing unit 12 adds these two reception signals. As a result, a signal from which fundamental harmonic components are eliminated and in which second harmonic components primarily remain is generated. After that, the B-mode processing unit 12 generates THI B-mode data or CHI B-mode data, by performing an envelope detection process or the like on the generated signal. In this situation, for example, when implementing the PM method with a CHI process, the B-mode processing unit 12 is able to generate B-mode data used for generating tissue image data, by performing a filtering process on the reception signal from the "1" transmission.

The B-mode processing unit 12 and the Doppler processing unit 13 illustrated in FIG. 1 are able to process both two-dimensional reflected-wave data and three-dimensional reflected-wave data. In other words, the B-mode processing unit 12 is able to generate two-dimensional B-mode data from two-dimensional reflected-wave data and to generate three-dimensional B-mode data from three-dimensional reflected-wave data. The Doppler processing unit 13 is able to generate two-dimensional Doppler data from two-dimensional reflected-wave data and to generate three-dimensional Doppler data from three-dimensional reflected-wave data.

The image generating unit 14 generates ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Further, from the two-dimensional Doppler data generated by the Doppler processing unit 13, the image generating unit 14 generates two-dimensional Doppler image data expressing moving member information. The two-dimensional Doppler image data is velocity image data, dispersion image data, power image data, or image data combining these types of image data.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. Specifically, the image generating unit 14 generates the display-purpose ultrasound image data by performing a coordinate transformation process compliant with the ultrasound scanning used by the ultrasound probe 1. Further, as various types of image processes other than the scan convert process, the image generating unit 14 performs, for example, an image process (a smoothing process) to re-generate a brightness-average image or an image process (an edge enhancement process) using a differential filter within images, while using a plurality of image frames obtained after the scan convert process is performed. Further, the image generating unit 14 superimposes additional information (text information of various parameters, scale marks, body marks, and the like) on the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data. The image generating unit 14 generates the "two-dimensional B-mode image data or two-dimensional Doppler image data" which is display-purpose two-dimensional ultrasound image data, from the "two-dimensional B-mode data or two-dimensional Doppler data" which is two-dimensional ultrasound image data before the scan convert process. For example, during a CHI process which implements the contrast echo method, the image generating unit 14 generates "two-dimensional contrast enhanced image data" as the "two-dimensional B-mode image data". During a CHI process, the image generating unit 14 may generate "two-dimensional tissue image data" as the "two-dimensional B-mode image data" if necessary.

Further, the image generating unit 14 generates three-dimensional B-mode image data by performing a coordinate transformation process on the three-dimensional B-mode data generated by the B-mode processing unit 12. Further, the image generating unit 14 generates three-dimensional Doppler image data by performing a coordinate transformation process on the three-dimensional Doppler data generated by the Doppler processing unit 13. The image generating unit 14 generates the "three-dimensional B-mode image data or three-dimensional Doppler image data" as the "ultrasound volume data". For example, when performing a CHI process, the image generating unit 14 generates "contrast enhanced volume data" as the "ultrasound volume data". During a CHI process, the image generating unit 14 may generate "contrast enhanced volume data" and "tissue volume data" as the "ultrasound volume data" if necessary.

Further, the image generating unit 14 performs a rendering process on the volume data, to generate various types of two-dimensional image data used for displaying the volume data on the monitor 2. Examples of the rendering process performed by the image generating unit 14 include a process to generate cross-sectional image data (Multi Planar Reconstruction [MPR] image data) from the volume data by implementing an MPR method. Other examples of the rendering process performed by the image generating unit 14 include a process to generate projection image data such as Volume Rendering (VR) image data or Maximum Intensity Projection (MIP) image data by performing a VR process or an MIP process. The projection image data is two-dimensional image data reflecting three-dimensional information.

The image memory 15 is a memory that stores therein the display-purpose image data generated by the image generating unit 14. After a diagnosis process, for example, the operator is able to invoke the image data stored in the image memory 15. Further, the image memory 15 is also able to store therein the data generated by the B-mode processing unit 12 or the Doppler processing unit 13. After a diagnosis process, for example, the operator is able to invoke the B-mode data or the Doppler data stored in the image memory 15. The invoked data is served as the display-purpose ultrasound image data by the image generating unit 14. Furthermore, the image memory 15 is able to store data output by the transmitting and receiving unit 11.

The detecting unit 16 detects the position of the needle tip of the puncture needle 5 by employing the position sensor 51 with which the puncture needle 5 is installed. In other words, by using information about a relative positional relationship between the base and the needle tip of the puncture needle 5 to which the position sensor 51 is attached, the detecting unit 16 detects the position of the needle tip of the puncture needle 5. Specifically, the detecting unit 16 receives the information about the magnetic field detected by the position sensor 51 installed on the base of the puncture needle 5, detects a three-dimensional position of the base of the puncture needle 5 based on the received information, and further detects the three-dimensional orientation of the puncture needle 5. For example, the detecting unit 16 detects the three-dimensional position of the base of the puncture needle 5 in a space having the transmitter 6 as the origin thereof. In other words, the detecting unit 16 detects three-dimensional coordinates of the needle tip in the real space. After that, based on the three-dimensional orientation of the puncture needle 5 and the length of the puncture needle 5, the detecting unit 16 detects the three-dimensional position of the needle tip of the puncture needle 5 in the space having the transmitter 6 as the origin thereof. In other words, the detecting unit 16 detects three-dimensional coordinates of the needle tip in the real space. Further, the detecting unit 16 is also able to detect the position of an insertion path of the puncture needle 5 in the real space, by sequentially detecting positions of the needle tip of the puncture needle 5 in the real space so as to detect a locus of the needle tip that moves within the three-dimensional space. The detection method described above can be used to detect the needle tip and the insertion path of the puncture needle 5, even if the puncture process using the puncture needle 5 is performed by hand. However, when the puncture process using the puncture needle 5 is performed while the puncture needle 5 is attached to the puncture adaptor 4, it is possible to obtain the orientation of the puncture needle 5 derived from the information about the puncture adaptor 4. For this reason, the detecting unit 16 is also able to detect the position of the base on the basis of the information detected by the position sensor 51 and to further detect the position of the needle tip by using the detected position of the base, the orientation of the puncture needle 5 derived from the information about the puncture adaptor 4, and the known length of the puncture needle 5. Further, in that situation also, the detecting unit 16 is also able to detect the position of the insertion path of the puncture needle 5 in the real space, by detecting the locus of the needle tip that moves in the three-dimensional space.

As long as the detecting unit 16 is able to detect the position of the needle tip of the puncture needle 5, the position sensor 51 may be installed in any arbitrary position of the puncture needle 5. Further, the position sensors 51 may be installed in a plurality of positions of the puncture needle 5. For example, as mentioned above, the position sensor 51 may be installed inside the needle tip of the puncture needle 5. In that situation, the detecting unit 16 receives the information about the magnetic field detected by the position sensor 51 installed inside the needle tip of the puncture needle 5 and detects the three-dimensional position of the needle tip of the puncture needle 5 based on the received information. The detecting unit 16 is thus able to detect the three-dimensional coordinates of the needle tip in the real space. Further, the detecting unit 16 is also able to detect the position of the insertion path of the puncture needle 5 in the real space, by sequentially detecting the positions of the needle tip of the puncture needle 5 in the real space so as to detect a locus of the needle tip that moves within the three-dimensional space. When detecting the position of the insertion path of the puncture needle 5 in the real space, a position sensor may be installed on the puncture needle 5 and the puncture adaptor 4.

The obtaining unit 17 obtains the position of a boundary of a region of interest that is set in first ultrasound image data of the subject P. In the first embodiment, the obtaining unit 17 obtains the position of the boundary of the region of interest that is set in the first ultrasound image data of the subject P into whom the puncture needle 5 is inserted, based on the position of the needle tip detected by the detecting unit 16. In this situation, the first ultrasound image data is ultrasound image data represented by tissue image data generated in an ordinary B-mode. For example, in the first embodiment, the first ultrasound image data is first ultrasound volume data generated by three-dimensionally scanning the subject P. The first ultrasound volume data is tissue volume data generated in the ordinary B-mode. Further, the region of interest described above is a treatment plan region in which an RFA treatment is to be performed and is three-dimensionally set in the first ultrasound volume data. In the first embodiment, the obtaining unit 17 obtains a three-dimensional position of the region of interest, based on the three-dimensional position of the needle tip detected by the detecting unit 16. Processes performed by the obtaining unit 17 based on detection results of the detecting unit 16 will be explained in detail later.

The internal storage unit 18 stores therein various types of data such as a control computer program (hereinafter, "control program") to execute ultrasound transmissions and receptions, image process, and display process, as well as diagnosis information (e.g., patients' IDs, doctors' observations), diagnosis protocols, and various types of body marks. Further, the internal storage unit 18 may also be used, as necessary, for storing therein any of the image data stored in the image memory 15. Further, it is possible to transfer the data stored in the internal storage unit 18 to an external peripheral apparatus via an interface circuit (not shown).

Further, for example, the internal storage unit 18 stores the angle at which the puncture needle 5 is attached to the puncture adaptor 4, as an insertion angle of the puncture needle 5. For example, when the puncture adaptor 4 is attached, the internal storage unit 18 stores an attachment angle "A" of the puncture adaptor 4, as an insertion angle "A" of the puncture needle 5. Further, the internal storage unit 18 according to the first embodiment stores one or more threshold values and setting information. The threshold values and the setting information stored in the internal storage unit 18 will be explained in detail later.

The controlling unit 19 controls the entire processes performed by the ultrasound diagnostic apparatus. Specifically, based on the various types of setting requests input by the operator by the input device 3 and various types of control programs and various types of data invoked from the internal storage unit 18, the controlling unit 19 controls processes performed by the transmitting and receiving unit 11, the B-mode processing unit 12, the Doppler processing unit 13, the image generating unit 14, the detecting unit 16, and the obtaining unit 17. Further, the controlling unit 19 exercises control so that the monitor 2 displays the ultrasound image data and the like stored in the image memory 15.

Figure 2:
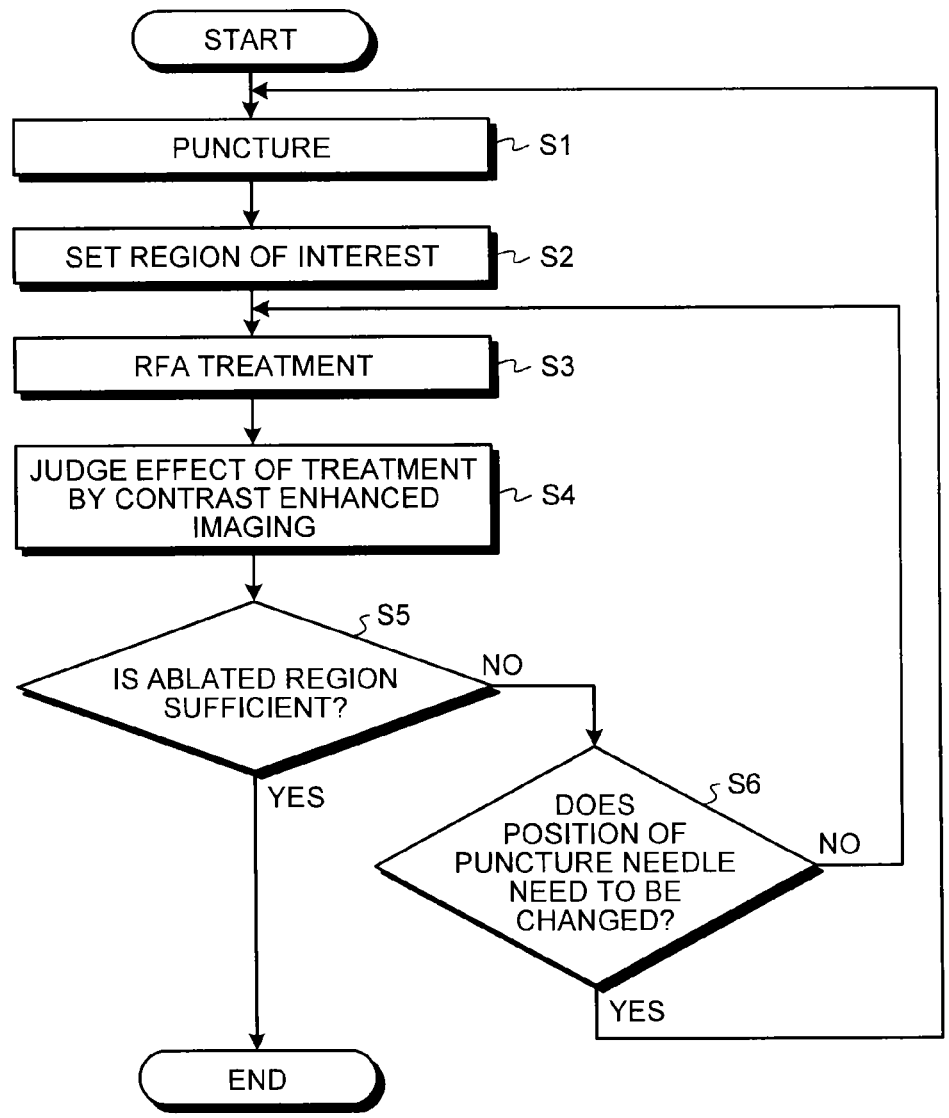
FIG. 2 is a flowchart of an exemplary workflow of an RFA treatment according to the first embodiment.

An overall configuration of the ultrasound diagnostic apparatus according to the first embodiment has thus been explained. The ultrasound diagnostic apparatus according to the first embodiment configured as described above implements, as described below, processes performed by the obtaining unit 17 based on detection results by the detecting unit 16 and processes performed by the image generating unit 14 based on processing results by the obtaining unit 17, for the purpose of promptly and conveniently judge the effect of a radiofrequency ablation treatment performed by using the puncture needle 5, without fail. First, an exemplary workflow of an RFA treatment according to the first embodiment will be explained, with reference to FIG. 2. FIG. 2 is a flowchart of the exemplary workflow of the RFA treatment according to the first embodiment.

First, a doctor performs a puncture process for an RFA treatment under the guide of ultrasound waves in an ordinary B-mode (step S1). At step s1, the image generating unit 14 generates first ultrasound volume data by a three-dimensional scan in the ordinary B-mode. After that, under the control of the controlling unit 19, the image generating unit 14 generates, for example, cross-sectional image data of an ordinary cross-sectional plane (an A plane) and cross-sectional image data of a cross-sectional plane in the depth direction containing the puncture needle 5, from the first ultrasound volume data. The doctor inserts the puncture needle 5 up to a treatment site of the subject P, while viewing the image data on the two cross-sectional planes that are displayed on the monitor 2 while being updated in a real-time manner under the control of the controlling unit 19.

For example, the controlling unit 19 is able to determine the cross-sectional plane that contains the puncture needle 5 in the first ultrasound volume data, based on the insertion angle "A" stored in the internal storage unit 18 and the three-dimensional relative positional relationship between the ultrasound probe 1 and the puncture adaptor 4. When the puncture process using the puncture needle 5 is performed by hand, the doctor is able to determine the cross-sectional plane in the depth direction containing the puncture needle 5, by designating a straight line that has a high brightness level while viewing the ultrasound image data on the A plane.

In the first embodiment, it is desirable to perform the following process, in order for the obtaining unit 17 to accurately obtain the position of the region of interest. In one example, by moving the ultrasound probe 1 on the body surface of the subject P, the doctor adjusts the position of the ultrasound probe 1 so that the treatment site (e.g., a tumor) is rendered in the cross-sectional image data of the A plane, and also, the A plane contains the insertion path of the puncture needle 5. After that, the doctor causes the needle tip of the puncture needle 5 attached to the puncture adaptor 4 to abut on the body surface of the subject P, while fixing the ultrasound probe 1 in the adjusted position. In this state, the doctor presses a confirm button included in the input device 3, for example. The detecting unit 16 determines the real-space position of the needle tip of the puncture needle 5 detected based on the information received from the position sensor 51 at the time when the confirm button was pressed as an initial position and informs the obtaining unit 17 of the initial position.

The obtaining unit 17 obtains the shape and the size of a three-dimensional scanned region and the three-dimensional relative positional relationship between the ultrasound probe 1 and the puncture adaptor 4, from the controlling unit 19. After that, based on the information obtained from the controlling unit 19, the obtaining unit 17 obtains information indicating "what position" in the space of the first ultrasound volume data (hereinafter, the "volume space"), the initial position detected by the detecting unit 16 corresponds to. As a result, the obtaining unit 17 associates the position of the needle tip in the real space with the position of the needle tip in the volume space.

If the orientation of the puncture needle 5 is derived from the information about the puncture adaptor 4 when the position of the needle tip is detected from the position of the base thereof or if the detecting unit 16 has detected the position of the needle tip by employing the position sensor 51 installed in the needle tip of the puncture needle 5, when the puncture process is performed by hand, the initial position in the volume space may be obtained, for example, as a result of the doctor viewing the ultrasound image data and designating an end of a straight line having a high brightness level, while the puncture needle 5 is inserted in the subject P up to the scanned region. Alternatively, for example, the initial position described above may be set by causing the needle tip or the base of the puncture needle 5 to abut on two end points of a transducer element arrangement plane of the ultrasound probe 1 that is arranged to abut on the body surface of the subject P. With this arrangement also, the obtaining unit 17 is able to associate the position in the real space with the position in the volume space.

In that state, when the doctor inserts the puncture needle 5 toward the treatment site, the detecting unit 16 detects the position of the needle tip and the moving path (the insertion path) of the puncture needle 5 in the real space and informs the obtaining unit 17 of the detecting results. Based on the correspondence relationship between the real space and the volume space, the obtaining unit 17 converts, in a real-time manner, the position of the needle tip and the insertion path detected in the real space by the detecting unit 16 into the position of the needle tip and the insertion path in the volume space. After that, under the control of the controlling unit 19 that received the information obtained by the obtaining unit 17, the image generating unit 14 generates the "cross-sectional image data of the A plane containing the puncture needle 5" and the "cross-sectional image data of the cross-sectional plane that is orthogonal to the cross-sectional image data of the A plane and that contains the insertion path of the puncture needle 5" at step S1.

Figure 3:
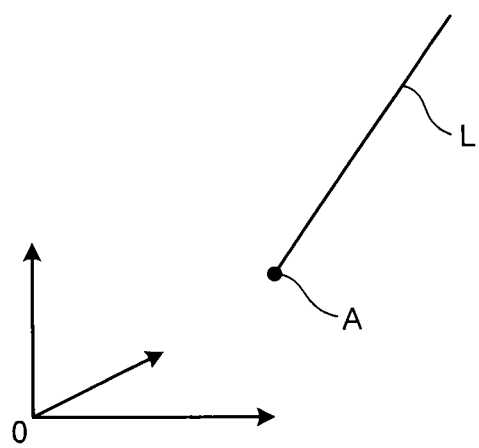
FIG. 3 is a drawing for explaining the detecting unit illustrated in FIG. 1.
Figure 5:
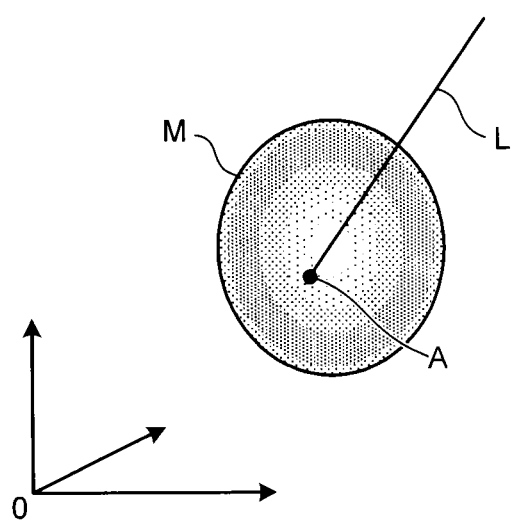

After that, the doctor sets a region of interest, which is a treatment plan region (step S2). FIG. 3 is a drawing for explaining the detecting unit illustrated in FIG. 1. FIGS. 4 and 5 are drawings for explaining the obtaining unit illustrated in FIG. 1. As illustrated in FIG. 3, the detecting unit 16 detects three-dimensional coordinates of a needle tip A of the puncture needle 5 in the real space, the puncture needle 5 being inserted up to substantially the center of the treatment site. Further, as illustrated in FIG. 3, the detecting unit 16 detects three-dimensional coordinates of an insertion path L of the puncture needle 5 in the real space.

Based on the information informed by the detecting unit 16, the obtaining unit 17 obtains the position of a point A' corresponding to the needle tip A and the position of a line L' corresponding to the insertion path L, in the first ultrasound volume data corresponding to the point at time when the puncture needle 5 has been inserted up to substantially the center of the treatment site. After that, as illustrated in the top section of FIG. 4, under the control of the obtaining unit 17, the image generating unit 14 generates cross-sectional image data of the A plane from the first ultrasound volume data and further generates image data by superimposing the point A' and the line L' on the generated cross-sectional image data. The monitor 2 displays the image data illustrated in the top section of FIG. 4. The doctor sets the region of interest in the image data illustrated in the top section of FIG. 4. For example, as illustrated in the bottom section of FIG. 4, the doctor sets a boundary M' of the region of interest in the vicinity of the point A', in such a manner that the region of interest contains a tumor T, which is the treatment site, and has a margin of approximately 5 mm.

In this situation, it is possible to estimate a shape of the boundary M' from the type of the puncture needle 5. For example, depending on whether the puncture needle 5 is of an expansion type or a single-needle type, the shape (the three-dimensional shape) of the boundary M' can be an ellipsoid or a sphere. In other words, a shape template of the region of interest is determined in accordance with the type of the puncture needle 5. For example, in the first embodiment, the internal storage unit 18 stores templates of various shapes corresponding to different types of the puncture needle 5. The doctor retrieves a template of the shape corresponding to the type of the puncture needle 5 from the internal storage unit 18 and causes the retrieved shape template to be displayed over the image data. After that, the doctor moves and adjusts the template and makes an enlargement/reduction adjustment thereon, so that the center of the template is positioned at the point A' and so that the boundary of the template has a margin of approximately 5 mm while the tumor T is contained therein. During the adjustment process, the axis of the template is set along the line L'. If one or more blood vessels are positioned near the tumor T, the doctor adjusts the template while taking the cooling effect of the bloodstream in the nearby blood vessels into consideration. The doctor has thus set the boundary M' of the region of interest.

After that, the obtaining unit 17 obtains the position of a boundary M in the real space as illustrated in FIG. 5, based on the relative positional relationship of the boundary M' with the needle tip A' in the volume space. In other words, as illustrated in FIG. 5, the obtaining unit 17 obtains the position of the boundary M of the region of interest in the real space, as well as the position of the needle tip A and the position of the insertion path L in the real space. The first embodiment is also applicable to a situation where the obtaining unit 17 automatically sets the boundary M' of the region of interest with respect to the position of the tumor T specified by the doctor. Alternatively, the first embodiment is also applicable to a situation where, for example, the obtaining unit 17 has the function of automatically detecting the tumor T based on brightness level information and automatically sets the boundary M' of the region of interest.

Returning to the description of FIG. 2, the doctor performs an RFA treatment on the region of interest set at step S2 (step S3). Specifically, the doctor performs the ablation treatment, while monitoring the temperature of the needle tip of the puncture needle 5, the output of radiofrequency, the impedance, and the like by using a treatment apparatus (not shown).

After that, the doctor judges the effect of the RFA treatment by performing a contrast enhanced imaging process (step S4). At step S4, the image generating unit 14 generates second ultrasound image data by using contrast enhanced image data of the subject P acquired after the treatment using the puncture needle 5 was performed, and the monitor 2 displays the generated second ultrasound image data. For example, after a predetermined time period (e.g., approximately five minutes) has passed since the treatment using the puncture needle 5, the doctor administers a contrast agent so as to check to see whether the bloodstream in the region of interest has disappeared, based on the second ultrasound image data generated from the contrast enhanced image data. In this situation, if the predetermined time period is approximately five minutes, the needle tip position of the puncture needle 5 and the abutted position of the ultrasound probe 1 are the same position as those observed when the first ultrasound volume data was generated. The second ultrasound image data will be explained in detail later.

Subsequently, the doctor judges whether the ablated region was sufficient by viewing the second ultrasound image data (step S5). In other words, the doctor judges whether an additional RFA treatment is necessary, because the ablated region is insufficient or because one or more tumor blood vessels remain. In this situation, if the ablated region is sufficient (step S5: Yes), the doctor ends the RFA treatment.

On the contrary, if the ablated region is not sufficient (step S5: No), the doctor judges whether the position of the puncture needle 5 needs to be changed, by viewing the second ultrasound image data (step S6). In this situation, if the position of the puncture needle 5 does not need to be changed (step S6: No), the procedure returns to step S3 where the doctor performs an additional RFA treatment. On the contrary, if the position of the puncture needle 5 needs to be changed (step S6: Yes), the procedure returns to step S1 where the doctor performs a puncture process to move the position of the puncture needle 5 so as to perform an additional RFA treatment and further performs the processes at step S2 and thereafter.

Next, the process performed by the ultrasound diagnostic apparatus according to the first embodiment at step S4 to judge the effect of the treatment will be explained in detail. First, the image generating unit 14 according to the first embodiment generates the second ultrasound image data by assigning a pixel value to each of pixels of which the change of the brightness value between before and after the contrast enhancement is equal to or larger than a threshold value with regard to the pre-contrast-enhancement image data and the post-contrast-enhancement image data of the subject P both of which were acquired after the treatment using the puncture needle 5 has been performed, the assigned pixel value corresponding to the distance between the pixel and the boundary of the region of interest. In the following sections, "the pre-contrast-enhancement image data and the post-contrast-enhancement image data" will be referred to as "contrast enhanced image data". To perform the process described above, the internal storage unit 18 according to the first embodiment stores "the threshold value for the change of the brightness value" and "setting information in which mutually-different pixel values are set depending on mutually-different distances from the boundary". Specifically, the internal storage unit 18 stores "color information in which mutually-different colors are set depending on the mutually-different distances from the boundary", as the setting information. More specifically, the internal storage unit 18 according to the first embodiment stores, as the setting information, the color information in which mutually-different colors in a first tone are set on the inside of the boundary depending on mutually-different distances from the boundary, whereas mutually-different colors in a second tone that is different from the first tone are set on the outside of the boundary depending on mutually-different distances from the boundary. Further, the internal storage unit 18 according to the first embodiment stores a uniform value (TH) as the threshold value for the change of the brightness value. The threshold value "TH" is a threshold value used for judging whether there is an inflow of the contrast agent.

After that, based on the setting information, the image generating unit 14 generates the second ultrasound image data. In the first embodiment, the image generating unit 14 generates the second ultrasound image data based on the color information. In other words, with regard to the contrast enhanced image data of the subject P acquired after the treatment using the puncture needle 5 has been performed, the image generating unit 14 generates the second ultrasound image data by assigning a color to each of pixels of which the change of the brightness value between before and after the contrast enhancement is equal to or larger than the threshold value "TH", the assigned color corresponding to the distance between the pixel and the boundary of the region of interest based on the color information. In this situation, in the first embodiment, the "contrast enhanced image data represented by the pre-contrast-enhancement image data and the post-contrast-enhancement image data" is contrast enhanced volume data generated by three-dimensionally scanning the subject P.

Accordingly, the image generating unit 14 according to the first embodiment generates, as the second ultrasound image data, second ultrasound volume data by assigning a voxel value to each of voxels of which the change of the brightness value between before and after the contrast enhancement is equal to or larger than the threshold value "TH" with regard to the contrast enhanced volume data, the assigned voxel value corresponding to the distance between the voxel and the boundary of the region of interest based on the setting information. Because the setting information is the color information described above, the image generating unit 14 generates, as the second ultrasound image data, the second ultrasound volume data by assigning a color to each of the voxels detected based on the threshold value, the assigned color corresponding to the distance between the voxel and the boundary of the region of interest based on the color information. As explained above, the contrast enhanced volume data is volume data generated by performing the three-dimensional scan using the ultrasound probe 1 that is in the same position as when the first ultrasound volume data was generated. In other words, it is possible to express each of the voxels in the contrast enhanced volume data by using three-dimensional coordinates in the same volume space as that of the voxels in the first ultrasound volume data.

In this situation, because the obtaining unit 17 is able to obtain the distance between each of the voxels structuring the contrast enhanced volume data and the boundary M', the obtaining unit 17 is able to obtain the distance between the real-space position of each of the voxels structuring the contrast enhanced volume data and the boundary M. Further, because the obtaining unit 17 is able to obtain the relative positional relationship between each of the voxels structuring the contrast enhanced volume data and the boundary M', the obtaining unit 17 is able to distinguish the inside of the region of interest from the outside of the region of interest in the volume space. Further, the obtaining unit 17 is able to judge whether the real-space position of each of the voxels structuring the contrast enhanced volume data is on the inside or on the outside of the region of interest. Thus, on the basis of the control of the obtaining unit 17, the image generating unit 14 generates the second ultrasound image data (the second ultrasound volume data). FIGS. 6A, 6B, and 7 to 10 are drawings for explaining the image generating unit according to the first embodiment.

Figure 6A:
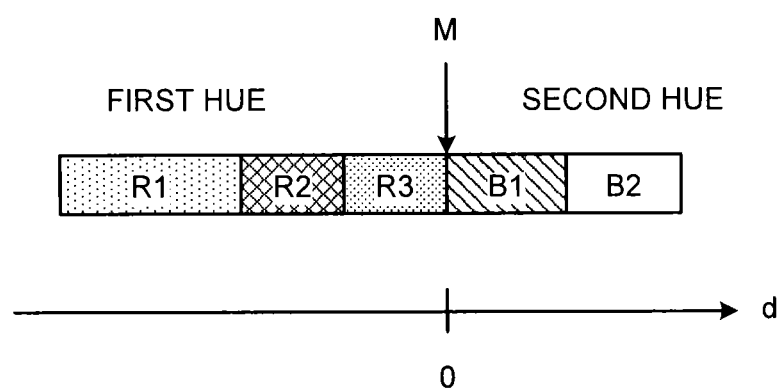
FIG. 6A, FIG. 6B, FIG. 7, FIG. 8, FIG. 9 and FIG. 10 are drawings for explaining an image generating unit according to the first embodiment.

For example, as illustrated in FIG. 6A, the color information stored in the internal storage unit 18 is associated with mutually-different colors depending on the mutually-different distances "d" from the boundary M of the region of interest. In the color information illustrated in FIG. 6A, the polarity is set so as to satisfy "d=0" on the boundary M of the region of interest, to satisfy "d<0" on the inside of the region of interest, and to satisfy "d>0" on the outside of the region of interest. Further, in the color information illustrated in FIG. 6A, when "d<0" is satisfied, tones "R1", "R2" and "R3" obtained by varying the lightness of a first hue are assigned corresponding to "absolute values of d". When "d>0" is satisfied, tones "B1" and "B2" obtained by varying the lightness of a second hue are assigned corresponding to "absolute values of d". For example, the first hue includes reddish colors, whereas the second hue includes bluish colors. Alternatively, the second hue may be on a gray scale. An inflow of the contrast agent to the inside of the region of interest means that the tumor remains. Thus, it is desirable to arrange the first hue to be a hue that calls the doctor's attention such as reddish colors. Although the color B2 is shown as white in FIGS. 6A, 6B, and so on for the sake of convenience in preparing the drawings, B2 is a lighter blue than B1 in actuality, for example.

Figure 6B:
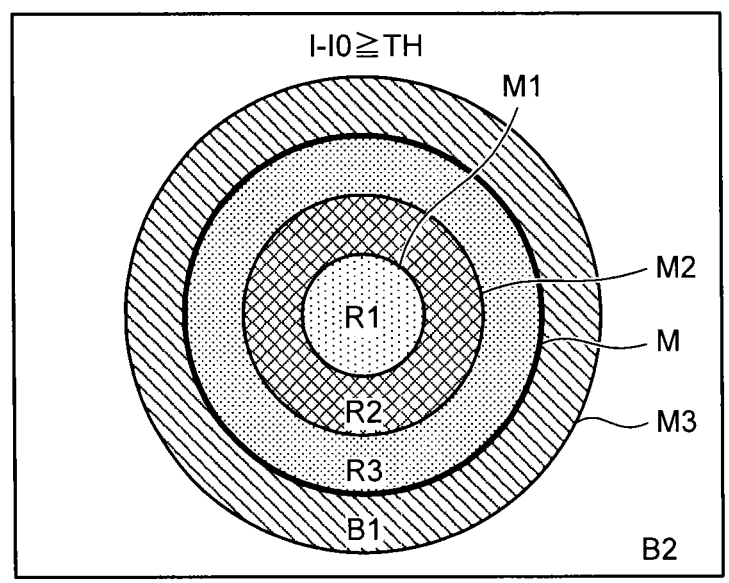

When such color information is used, if the region of interest is a sphere, for example, a spherical boundary M1 and a spherical boundary M2 are set on the inside of the region of interest, whereas a spherical boundary M3 is set on the outside of the region of interest, corresponding to the distances from the boundary M of the region of interest, as illustrated in FIG. 6B.

The obtaining unit 17 obtains the brightness value of each of the voxels structuring the pre-contrast-enhancement volume data (e.g., the ultrasound volume data obtained by implementing the contrast echo method at the point at the time when the region of interest was set) as a pre-contrast-enhancement brightness value "I0". After that, the obtaining unit 17 obtains a brightness value "I" of each of the voxels structuring the contrast enhanced volume data, which is the post-contrast-enhancement image data generated by implementing the contrast echo method. In other words, because the first ultrasound volume data is the data obtained by using the B-mode, the first ultrasound volume data is not suitable as a comparison target to be compared with the contrast enhanced volume data generated by implementing the contrast echo method. For this reason, it is desirable to acquire the ultrasound volume data by implementing the contrast echo method after the region of interest is set (e.g., before the contrast agent is administered) and to use the acquired volume data as the pre-contrast-enhancement image data, which serves as a comparison target to be compared with the contrast enhanced volume data generated by implementing the contrast echo method after the contrast agent is administered. After that, the obtaining unit 17 calculates a change of the brightness value "I−I0" for each of the voxels and monitors the calculated values. For example, the obtaining unit 17 monitors the change of the brightness value for each of all the voxels. After that, the obtaining unit 17 converts the position of each of voxels that satisfy "I−I0≥TH" into a position in the real space and obtains the distance and the positional relationship between the real-space position of each of voxels and the boundary M. Subsequently, the obtaining unit 17 obtains the colors corresponding to the obtained distances and positional relationships, from the color information illustrated in FIG. 6A and exercises control so that the image generating unit 14 generates the volume data by assigning the obtained colors.

For example, as illustrated in FIG. 6B, if the real-space position of a voxel satisfying "I−I0≥TH" is on the inside of the boundary M1, the image generating unit 14 assigns the tone "R1" to the voxel. As another example, as illustrated in FIG. 6B, if the real-space position of a voxel satisfying "I−I0≥TH" is between the boundary M1 and the boundary M2, the image generating unit 14 assigns the tone "R2" to the voxel. As yet another example, as illustrated in FIG. 6B, if the real-space position of a voxel satisfying "I−I0≥TH" is between the boundary M2 and the boundary M, the image generating unit 14 assigns the tone "R3" to the voxel.

As yet another example, as illustrated in FIG. 6B, if the real-space position of a voxel satisfying "I−I0≥TH" is between the boundary M and the boundary M3, the image generating unit 14 assigns the tone "B1" to the voxel. As yet another example, as illustrated in FIG. 6B, if the real-space position of a voxel satisfying "I−I0≥TH" is on the outside of the boundary M3, the image generating unit 14 assigns the tone "B2" to the voxel.

Figure 7:
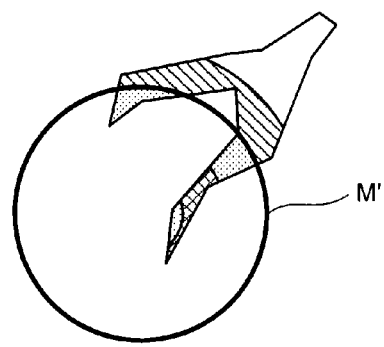

As a result of these processes, the image generating unit 14 generates the second ultrasound volume data illustrated in FIG. 7. For example, as illustrated in FIG. 7, the image generating unit 14 generates the second ultrasound volume data in which the boundary M' is superimposed. Although the second ultrasound volume data illustrated in FIG. 7 appears to be two-dimensional image data for the sake of convenience in preparing the drawing, the second ultrasound volume data is three-dimensional image data in actuality. Further, the threshold value described above is a value that is empirically determined by a doctor or the like, for example. Further, in the above example, the value corresponding to the change of the brightness value is set as the threshold value for the change of the brightness value. However, the first embodiment is also applicable to a situation where, as the threshold value for the change of the brightness value, a value (e.g., 5 decibels [dB]) indicating the degree of the change of the brightness value is set. In that situation, for example, the obtaining unit 17 converts "I−I0" into a decibel value based on a gamma curve used for outputting images to the monitor 2 and performs a comparing process between the converted decibel value and the threshold value.

When the contrast echo method is implemented, the contrast enhanced volume data is generated in chronological order. Under the control of the obtaining unit 17, the image generating unit 14 may generate a piece of second ultrasound volume data every time a piece of contrast enhanced volume data is generated or may generate the second ultrasound volume data by using all the voxels of which the change of the brightness value is equal to or larger than the threshold value, from among all the pieces of contrast enhanced volume data generated during the contrast enhancement time period.

In other words, the first embodiment is applicable to a situation where the second ultrasound volume data is generated in chronological order and to a situation where sustaining-type second ultrasound volume data is generated in which the positions of all the voxels that represent a value equal to or larger than the threshold value during the contrast enhancement period are sustained. Further, the first embodiment is also applicable to a situation where the contrast enhancement period is divided into a plurality of sections so that sustaining-type second ultrasound volume data is generated in which the positions of all the voxels that represent a value equal to or larger than the threshold value are sustained, for each of the sectioned periods.

After that, the controlling unit 19 causes the monitor 2 to display the second ultrasound image data. In the first embodiment, because the second ultrasound image data is generated as the volume data (the second ultrasound volume data), the controlling unit 19 causes the monitor 2 to display one or both of cross-sectional image data and projection image data that are generated from the second ultrasound volume data.

Figure 8:
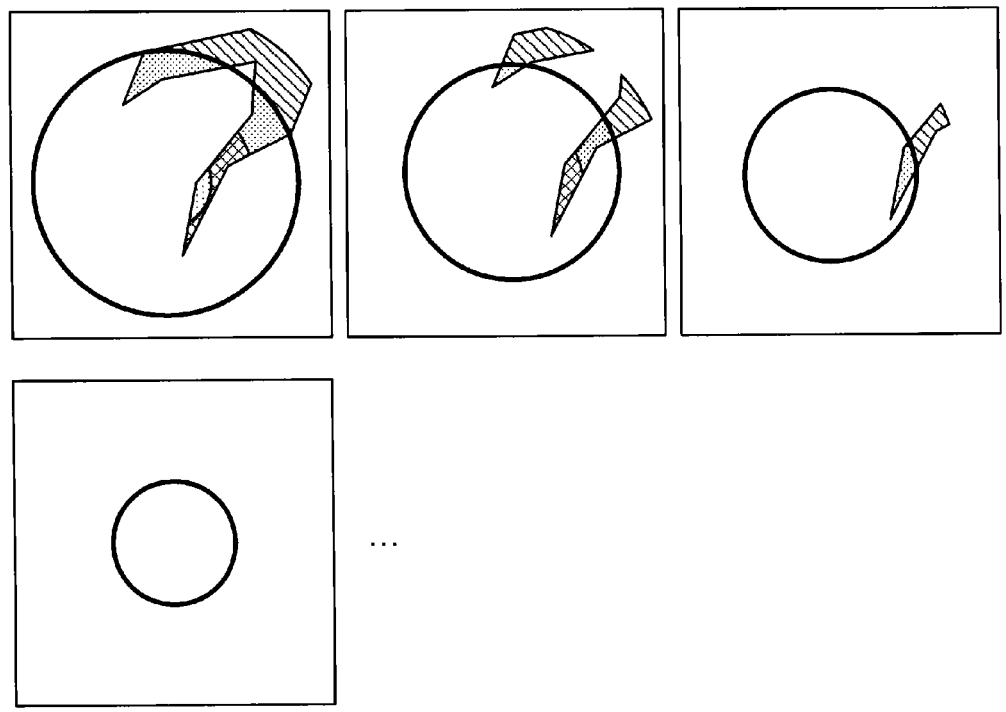
Figure 9:
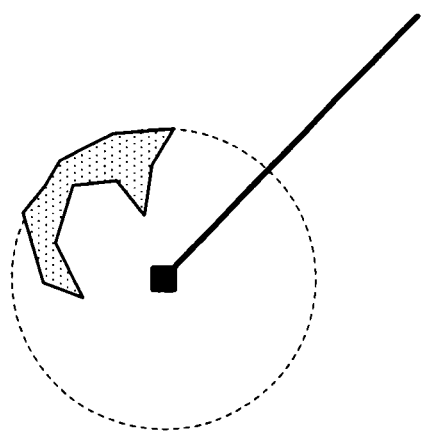
Figure 10:
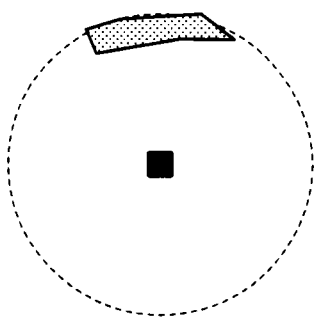

For example, under the control of the controlling unit 19, the image generating unit 14 cuts off the second ultrasound volume data illustrated in FIG. 7 on a plurality of A planes along the depth direction. As a result, as illustrated in FIG. 8, the image generating unit 14 generates pieces of MPR image data on the plurality of A planes. The monitor 2 displays the plurality of pieces of MPR image data illustrated in FIG. 8. If a tumor blood vessel is spatially inhomogeneous or if a relatively large blood vessel has the cooling effect, there is a possibility that the ablation may have not been performed as planned. To cope with this situation, by causing the plurality of cross-sectional planes to be displayed as illustrated in FIG. 8, the doctor is able to judge the effect on the multiple cross-sectional planes.

Alternatively, the controlling unit 19 may cause the second ultrasound image data to be displayed while being limited to the region of interest. Alternatively, the controlling unit 19 may cause the position of the puncture needle 5 to be displayed while being superimposed on the second ultrasound image data limited to the region of interest. In the first embodiment in which the second ultrasound image data is generated as the second ultrasound volume data, under the control of the controlling unit 19, the image generating unit 14 extracts the volume data of the inside of the region of interest from the second ultrasound volume data and generates projection image data by projecting the extracted volume data in a predetermined direction. The projection image data is VR image data or MIP image data. For example, the image generating unit 14 generates the MIP image data illustrated in FIG. 9 by performing an MIP process on the volume data obtained by superimposing the point A' and the line L' described above onto the extracted volume data.

Alternatively, the controlling unit 19 may cause cross-sectional image data to be displayed, the cross-sectional image data being obtained by cutting off the second ultrasound volume data on a cross-sectional plane in the second ultrasound volume data that contains the needle tip of the puncture needle 5 and that is orthogonal to the insertion path of the puncture needle 5. In this situation, the controlling unit 19 may arrange the cross-sectional image data to be cross-sectional image data limited to the region of interest. For example, under the control of the controlling unit 19, the image generating unit 14 extracts the volume data corresponding to the inside of the region of interest from the second ultrasound volume data. Further, the obtaining unit 17 obtains the position of the cross-sectional plane that contains the point A' described above and is orthogonal to the line L', in the extracted volume data. The image generating unit 14 then generates the MPR image data illustrated in FIG. 10 by cutting off the extracted volume data on the cross-sectional plane obtained by the obtaining unit 17. A dotted-line circle corresponding to the boundary M' is superimposed on each of the pieces of image data illustrated in FIGS. 9 and 10. These dotted lines are rendered by the image generating unit 14.

The display-purpose image data displayed on the monitor 2 is not limited to the two-dimensional image data generated from the second ultrasound volume data described above. For example, the controlling unit 19 may cause the monitor 2 to display image data obtained by superimposing together the two-dimensional image data generated from the second ultrasound volume data, with at least one selected from the following: ultrasound image data rendering a tissue of the subject P; and ultrasound image data rendering a contrast agent distribution in the subject P. The ultrasound image data rendering a tissue of the subject P is, for example, fundamental harmonic volume data generated from the three-dimensional reflected-wave data from which the first ultrasound volume data or the contrast enhanced volume data is generated. Further, the ultrasound image data rendering a contrast enhanced tissue of the subject P is the contrast enhanced volume data used for generating the second ultrasound volume data.

For example, according to a position alignment instruction from the obtaining unit 17, the image generating unit 14 generates superimposed image data by performing an MPR process, a VR process, an MIP process, or the like while using volume data in which the second ultrasound volume data is combined with volume data served as a target of the superimposition. For example, the image generating unit 14 combines the volume data after lowering the opacity of the volume data served as the target of the superimposition.

When a plurality of pieces of second ultrasound volume data are generated in chronological order, the various types of display-purpose image data described above are each generated from the pieces of second ultrasound volume data. In another example, when one piece of sustaining-type second ultrasound volume data is generated, the various types of display-purpose image data described above are generated from the one piece of second ultrasound volume data. In yet another example, when a plurality of pieces of sustaining-type second ultrasound volume data are generated, the various types of display-purpose image data described above are generated from each of the plurality of pieces of second ultrasound volume data.

As described above, the second ultrasound image data is the image data provided so as to make it possible for the doctor who judges the effect of the treatment to understand the positional relationship between the bloodstream that remains after the ablation treatment and the boundary of the region of interest. In the description above, the example is explained in which the color information in which the mutually-different colors are set corresponding to the mutually-different distances from the boundary is used as the setting information used for generating the image data. However, the setting information used for presenting the positional relationship between the bloodstream that remains after the ablation treatment and the boundary of the region of interest is not limited to the color information described above. For example, the setting information in which the mutually-different pixel values are set according to the mutually-different distances from the boundary may be hatching information in which mutually-different hatchings are set according to the mutually-different distances from the boundary. Alternatively, the setting information may be shade-level information in which mutually-different levels of shade of similar colors are set according to mutually-different distances from the boundary. For example, the shade-level information may be shade-level information in which mutually-different levels of gradation in a gray scale are set according to mutually-different distances from the boundary.

Figure 11:
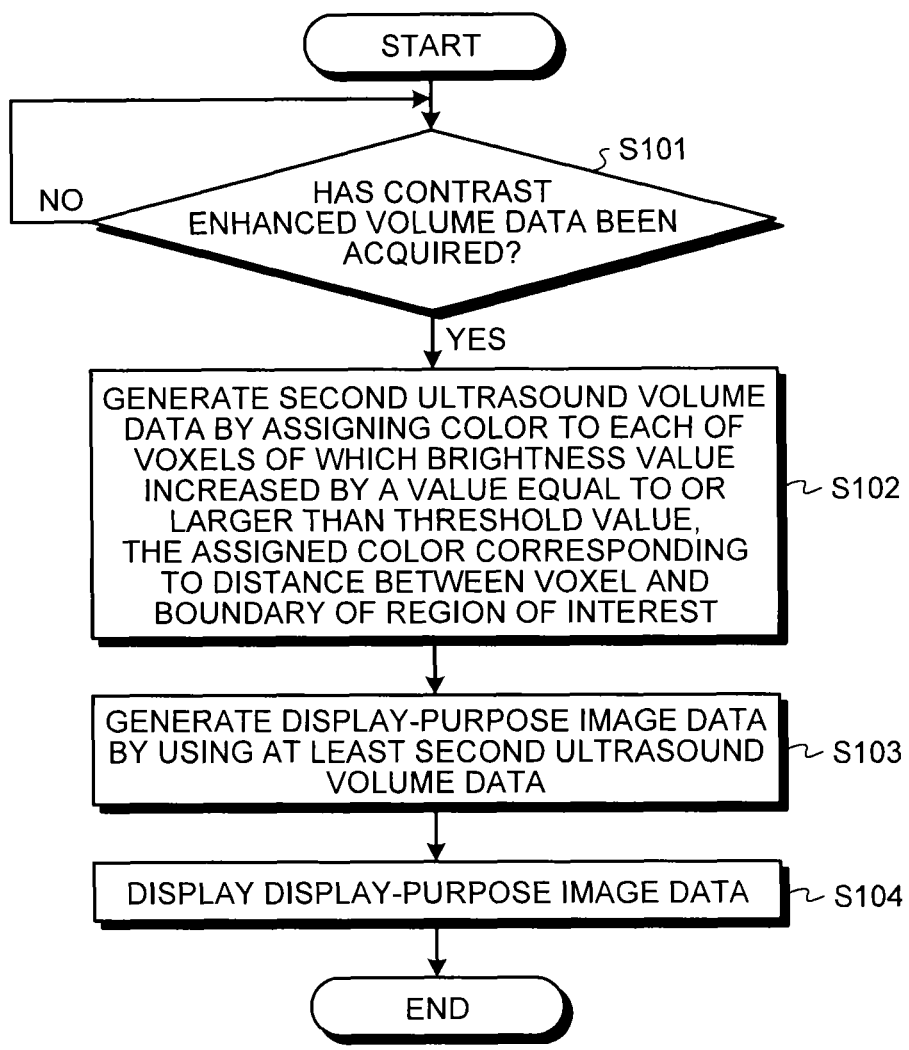
FIG. 11 is a flowchart of an example of a process performed by the ultrasound diagnostic apparatus according to the first embodiment.

Next, an example of a process performed by the ultrasound diagnostic apparatus according to the first embodiment will be explained, with reference to FIG. 11. FIG. 11 is a flowchart of the example of the process performed by the ultrasound diagnostic apparatus according to the first embodiment. FIG. 11 is a flowchart of the example of the process performed by the ultrasound diagnostic apparatus at step S4 illustrated in FIG. 2.

As illustrated in FIG. 11, the obtaining unit 17 included in the ultrasound diagnostic apparatus according to the first embodiment judges whether contrast enhanced volume data has been acquired (step S101). If no contrast enhanced volume data has been acquired (step S101: No), the obtaining unit 17 waits until contrast enhanced volume data is acquired.

On the contrary, if contrast enhanced volume data has been acquired (step S101: Yes), the obtaining unit 17 obtains the position of the region of interest in the contrast enhanced volume data. After that, under the control of the obtaining unit 17, the image generating unit 14 generates second ultrasound volume data by assigning a color to each of voxels of which the brightness value increased by a value equal to or larger than the threshold value, the assigned color corresponding to the distance between the voxel and the region of interest (step S102).

Subsequently, under the control of the controlling unit 19, the image generating unit 14 generates display-purpose image data that uses at least the second ultrasound volume data (step S103). After that, under the control of the controlling unit 19, the monitor 2 displays the display-purpose image data (step S104), and the process ends.

As explained above, in the first embodiment, by detecting the position of the needle tip accurately and conveniently by the position sensor 51, it is possible to accurately and conveniently obtain the position of the set boundary of the set region of interest based on position of the needle tip and the type of the puncture needle 5, in the real space and in the volume space. Further, in the first embodiment, the criterion for the color map (the color information) is set at the boundary of the region of interest (the boundary of the treatment plan region). Thus, it is possible to promptly generate and display the display-purpose image data in which the inflows of the contrast agent to the inside of the treatment plan region and to the vicinity of the treatment plan region are emphasized with the mutually-different hues, based on the accurately-obtained position of the boundary of the region of interest. Further, by viewing the display-purpose image data in which the inflows of the contrast agent are emphasized with the mutually-different hues, the doctor is able to visually recognize easily the sites where the bloodstream remains. As a result, according to the first embodiment, it is possible to promptly and conveniently judge the effect of the radiofrequency ablation treatment, without fail.

The first embodiment may be implemented in modification examples described below. FIGS. 12A, 12B, 13A, and 13B are drawings for explaining modification examples of the first embodiment.

Figure 12A:
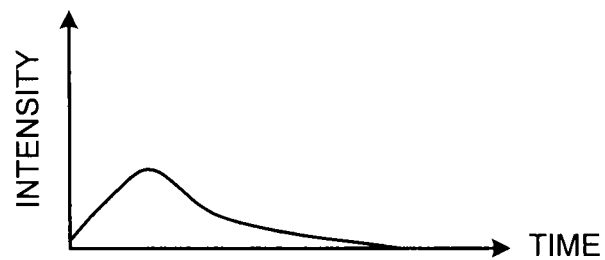
FIG. 12A, FIG. 12B, FIG. 13A and FIG. 13B are drawings for explaining modification examples of the first embodiment.

In a first modification example, the controlling unit 19 further causes a temporal change curve to be displayed so as to indicate changes in the brightness values of the region of interest over the course of time. In other words, because the plurality of pieces of contrast enhanced volume data are generated in chronological order, the controlling unit 19 is able to generate a temporal change curve corresponding to the inside of the region of interest, for example. Thus, as illustrated in FIG. 12A, the controlling unit 19 generates a temporal change curve by plotting the brightness levels ("intensity") in the region of interest in relation to time ("time") and causes the generated temporal change curve to be displayed together with the image data. In this situation, the controlling unit 19 may generate one temporal change curve by plotting an average brightness value in the region of interest or may generate a plurality of temporal change curves by plotting brightness values of each of the plurality of voxels in the region of interest. Alternatively, the controlling unit 19 may generate a plurality of temporal change curves by plotting an average brightness value in each of a plurality of regions in the region of interest (e.g., the region inside the boundary M1, the region between the boundary M1 and the boundary M2, and the region between the boundary M2 and the boundary M). Further, the controlling unit 19 may generate a temporal change curve for the outside of the region of interest.

Figure 12B:
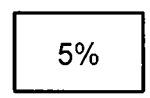

Alternatively, in the first modification example, the controlling unit 19 may further cause a ratio to be displayed, the ratio being a ratio of the region to which the pixel values have been assigned within the region of interest, to the region of interest. When the color information is used as the setting information, the controlling unit 19 causes a ratio to be displayed, the ratio being a ratio of the region in which colors have been assigned within the region of interest, to the region of interest. For example, the controlling unit 19 may calculate the ratio by dividing the number of voxels in the region of interest of which the change of the brightness value is equal to or larger than the threshold value by the number of voxels in the region of interest, so that the monitor 2 displays the calculated ratio. For example, as illustrated in FIG. 12B, the controlling unit 19 may calculate a ratio "5%" of the contrast agent inflow volume in the region of interest, to the volume of the region of interest, so that the monitor 2 displays the calculated ratio. The ratio may be calculated with respect to the entirety of the region of interest or may be calculated with respect to each of a plurality of regions in the region of interest. Further, the controlling unit 19 may calculate a ratio for a region on the outside of the region of interest. Furthermore, when a plurality of pieces of second ultrasound volume data are generated, the ratio can be calculated from each of the pieces of the second ultrasound volume data.

By viewing the temporal change curve or the ratio described above, the doctor is further able to objectively and efficiently judge the effect of the RFA treatment.

Figure 13A:
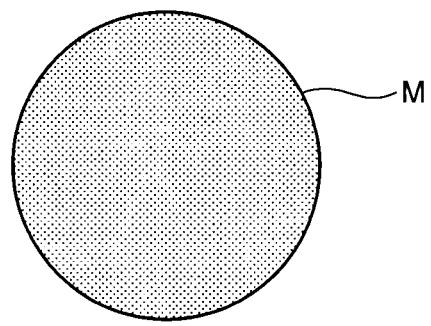
Figure 13B:
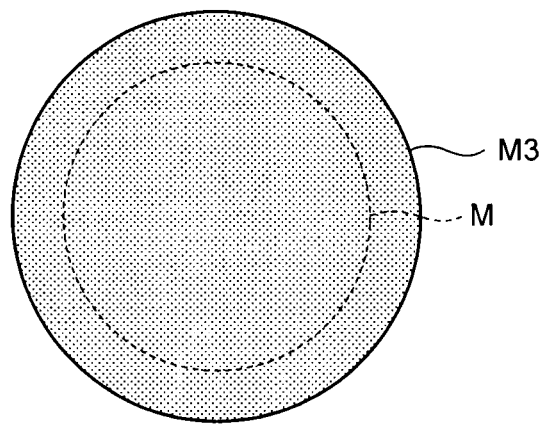

In a second modification example, the image generating unit 14 generates the second ultrasound image data for the inside of the region of interest or for a limited region that is limited to the inside of the region of interest and a region outside the region of interest positioned near the boundary. For example, as illustrated in FIG. 13A, the obtaining unit 17 exercises control so that the image generating unit 14 generates second ultrasound volume data limited to the inside of the boundary M. Alternatively, as illustrated in FIG. 13B, the image generating unit 14 may generate second ultrasound volume data limited to the inside of the boundary M3, which is the boundary positioned outside the boundary M. In other words, in the second modification example, by limiting the region monitored for increases of the brightness levels caused by the contrast agent, it is possible to reduce the load in the process of generating the second ultrasound volume data.

The processes explained in the first embodiment may be performed without employing the position sensor 51 and the detecting unit 16. As explained above, the second ultrasound volume data, which is the image data used for judging the effect of the treatment, is generated based on the setting information that is set based on the distances in the real space. In other words, the image generating unit 14 is able to generate second ultrasound volume data as long as it is possible to convert distances in the volume space into distances in the real space. In this situation, the controlling unit 19 that controls the transmitting and receiving unit 11, the B-mode processing unit 12, and the image generating unit 14 is able to obtain a correspondence relationship between the shape and the size of the ultrasound scanned region and the shape and the size of the ultrasound image data. Further, the controlling unit 19 is also able to obtain conversion information used for converting the distances in the volume space into the distances in the real space, based on the correspondence relationship.

Accordingly, for example, the obtaining unit 17 obtains the conversion information described above from the controlling unit 19. After that, for example, by using the obtained conversion information, the obtaining unit 17 converts the distance between the boundary and each of pixels of which the change of the brightness value is equal to or larger than the threshold value, into a distance in the real space. Subsequently, the obtaining unit 17 obtains a color to be assigned to each of the pixels based on the distances resulting from the conversion. By performing this process, the image generating unit 14 is also able to generate and display the second ultrasound volume data described above.

Second Embodiment

Figure 14:
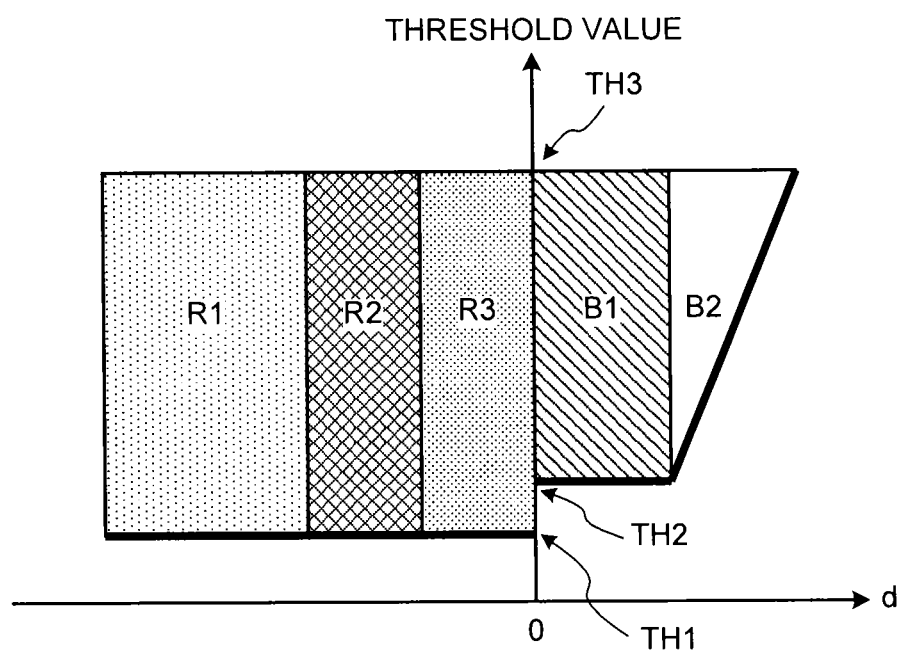
FIG. 14 is a drawing for explaining a second embodiment.

In the first embodiment, the example is explained in which the threshold value used for judging the increases of the brightness values is the uniform value, when the information related to the inflows of the contrast agent to the inside and to the outside of the region of interest (the treatment plan region) is displayed while being emphasized by the color information in which the colors are assigned corresponding to the distances from the boundary. In a second embodiment, an example in which the threshold value used for judging the increases of the brightness values caused by the contrast agent is not uniform will be explained, with reference to FIG. 14. FIG. 14 is a drawing for explaining the second embodiment.

As threshold values for changes of the brightness values, the internal storage unit 18 according to the second embodiment stores a plurality of threshold values that are mutually different depending on mutually-different distances from the boundary. For example, as illustrated in FIG. 14, the internal storage unit 18 stores information in which a uniform threshold value "TH1" is set for the inside of the region of interest which has the distance "d<0" and to which the tones "R1, R2, and R3" are assigned as illustrated in FIG. 6A. Further, for example, as illustrated in in FIG. 14, the internal storage unit 18 stores information in which a uniform threshold value "TH2" that is larger than TH1 is set for a part of the outside of the region of interest which has the distance "d>0" and to which the tone "B1" is assigned as illustrated in FIG. 6A.

Further, for example, as illustrated in FIG. 14, the internal storage unit 18 stores information in which threshold values increasing from TH2 to TH3 according to a linear function in proportion to the value of d are set for another part of the outside of the region of interest which has the distance "d<0" and to which the tone "B2" is assigned as illustrated in FIG. 6A. The threshold values corresponding to the distances may be arbitrarily set by the operator.

After that, the image generating unit 14 according to the second embodiment generates second ultrasound image data by assigning a color to each of pixels of which the value is equal to or larger than the threshold value corresponding to the distance thereof from the boundary of the region of interest, the assigned color corresponding to the distance between the pixel and the boundary of the region of interest, based on the basis of the color information. Like in the first embodiment, a three-dimensional scan is performed in the second embodiment. Accordingly, the image generating unit 14 according to the second embodiment generates the second ultrasound volume data by assigning a color to each of voxels of which the value is equal to or larger than the threshold value corresponding to the distance thereof from the boundary of the region of interest, the assigned color corresponding to the distance between the voxel and the boundary of the region of interest, based on the color information. In the second embodiment also, the image generating unit 14 may generate the second ultrasound volume data by assigning the pixel values corresponding to the distances from the boundary, by using setting information (e.g., hatching information, shade-level information) other than the color information.

After that, in the second embodiment also, the display-purpose image data, the temporal change curve, and the ratio described in the first embodiment are displayed. Except for the configuration in which the threshold values vary depending on the distances from the boundary, the explanation of the first embodiment is also applied to the second embodiment. Further, the processes performed by the ultrasound diagnostic apparatus according to the second embodiment are the same as those in the first embodiment except that, for example, the process at step S102 in FIG. 11 is performed as the judgment process with the threshold values using the setting information illustrated in FIG. 14. Thus, the explanation will be omitted.

To judge the effect of the RFA treatment, whether there is an inflow of the contrast agent on the inside of the region of interest is important. However, even on the outside of the region of interest, if there is a relatively large blood vessel in the vicinity, the blood vessel may have a cooling effect and may have an influence on the treatment. The setting information illustrated in FIG. 14 is an example of a color map that can improve the visibility of a relatively large blood vessel that is positioned near the outside of the region of interest.

According to the second embodiment, by using the color map, it is possible to provide the information that can help the doctor to check if a region of interest is appropriately set and to plan additional treatments, by emphatically displaying a blood vessel that is positioned on the outside of the region of interest but has a large increase in the brightness levels. The second embodiment is also applicable to a situation where a plurality of threshold values is set depending on distances even on the inside of the region of interest.

Third Embodiment

Figure 15A:
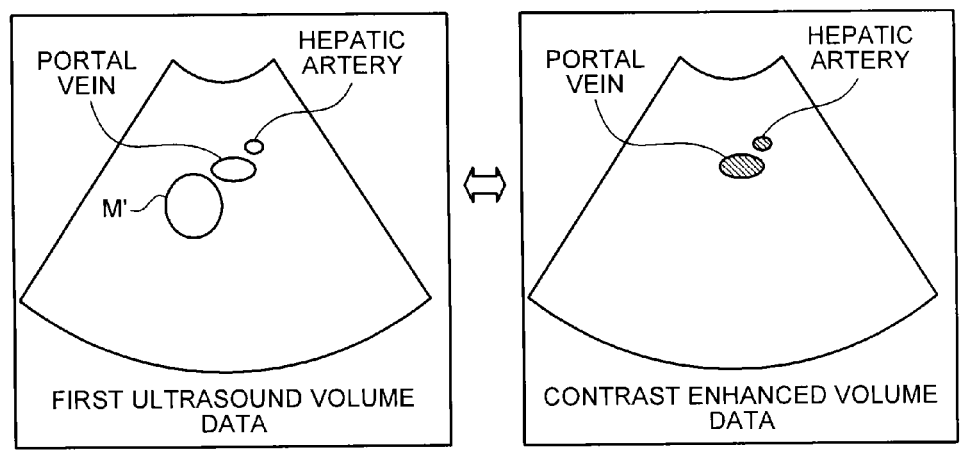
FIG. 15A and FIG. 15B are drawings for explaining a third embodiment.
Figure 15B:
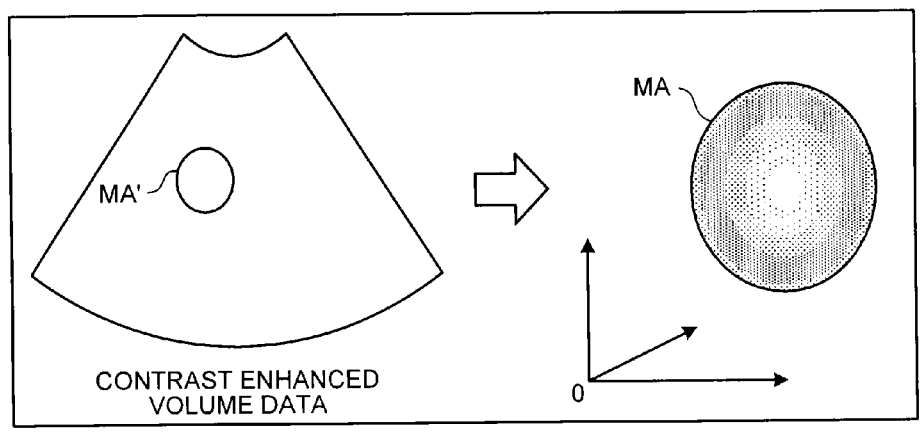

In a third embodiment, a process that is performed when contrast enhanced image data (contrast enhanced volume data) is acquired after the puncture needle 5 is pulled out will be explained, with reference to FIGS. 15A and 15B. FIGS. 15A and 15B are drawings for explaining the third embodiment.

Specifically, in the first and the second embodiments, the example is explained in which, at step S4 in FIG. 2, the contrast enhanced volume data is acquired while the position of the puncture needle 5 is fixed. In that situation, it is possible to uniquely identify the positional relationship between the first volume data and the contrast enhanced volume data. However, the process of judging the effect of an RFA treatment may be performed not only a short time later (e.g., five minutes later) but also a number of days later (e.g., five days later). In that situation, the doctor is required to judge the effect of the treatment and to make the judgment at steps S5 and S6, by using contrast enhanced volume data that is acquired while the puncture needle 5 is not inserted.

To cope with this situation where the contrast enhanced image data (contrast enhanced volume data) is acquired after the puncture needle 5 has been pulled out, the obtaining unit 17 according to the third embodiment performs a position aligning process between the first ultrasound image data (the first ultrasound volume data) and the contrast enhanced image data (the contrast enhanced volume data). After that, based on a result of the position aligning process, the obtaining unit 17 according to the third embodiment obtains the position of a corresponding region in the contrast enhanced image data (the contrast enhanced volume data) that corresponds to the region of interest. Specifically, the obtaining unit 17 performs the position aligning process based on a structure rendered in the surrounding area of the region of interest in the first ultrasound image data (the first ultrasound volume data).

For example, as illustrated in FIG. 15A, the obtaining unit 17 obtains, from the first ultrasound volume data, the position of a portal vein or a hepatic artery that is positioned near the boundary M' corresponding to the boundary M of the region of interest. For example, the position of the portal vein or the hepatic artery in the first ultrasound volume data may be specified by a doctor or a technician or may be obtained by the obtaining unit 17 based on information about brightness values. After that, the obtaining unit 17 obtains the position of the portal vein or the hepatic artery in the contrast enhanced volume data. For example, the position of the portal vein or the hepatic artery in the contrast enhanced volume data may be specified by a doctor or a technician or may be obtained by the obtaining unit 17 based on information about brightness values.

Accordingly, the obtaining unit 17 performs the position aligning process between the first ultrasound volume data and the contrast enhanced volume data. Alternatively, the obtaining unit 17 may perform an initial position aligning process between the first ultrasound volume data and the contrast enhanced volume data by using position information of a structure such as a blood vessel while employing a position sensor and may further complete aligning the two types of volume data with each other, by moving one of the two types of volume data slightly.

Specifically, when contrast enhanced volume data is acquired after the puncture needle 5 has been pulled out, the doctor arranges the puncture needle 5 provided with the position sensor 51 in such a manner that, for example, the needle tip of the puncture needle 5 abuts on the body surface of the subject on which the ultrasound probe 1 is abutting, for the purpose of accurately performing the position aligning process. The position in which the ultrasound probe 1 abuts on the body surface when the contrast enhanced volume data is acquired is usually adjusted so as to be the position in which the first ultrasound volume data was acquired. With this arrangement, the detecting unit 16 detects the position of the needle tip. It is desirable to arrange the position in which the needle tip abuts on the body surface at this time, so as to be substantially the same as the position of the body surface in which the puncture needle 5 was inserted during the puncture process of the treatment. As a result, the obtaining unit 17 is able to obtain the position of the needle tip at the time of the acquisition of the contrast enhanced volume data. In this situation, the obtaining unit 17 is able to, as described above, obtain the position on the body surface in which the puncture needle 5 was inserted during the RFA treatment. The obtaining unit 17 corrects the initial position alignment by using the position information before and after the treatment detected by the detecting unit 16. As a result, the obtaining unit 17 is able to accurately perform the position aligning process between the first ultrasound volume data and the contrast enhanced volume data.

Alternatively, for example, the doctor may acquire the contrast enhanced volume data after the puncture needle 5 is pulled out, by using the ultrasound probe 1 to which a position sensor is attached. The detecting unit 16 is able to detect the abutment position of the ultrasound probe 1, by using the position sensor attached to the ultrasound probe 1. Thus, the obtaining unit 17 is able to accurately perform the position aligning process between the first ultrasound volume data and the contrast enhanced volume data, based on the insertion position of the puncture needle 5 at the time of the acquisition of the first ultrasound volume data and the abutment position of the ultrasound probe 1 at the time of the acquisition of the contrast enhanced volume data. Further, when using the abutment position of the ultrasound probe 1 at the time of the acquisition of the contrast enhanced volume data, it is also acceptable to attach a position sensor to the ultrasound probe 1 even at the time of the acquisition of the first ultrasound volume data. With this arrangement also, the obtaining unit 17 is able to accurately perform the position aligning process between the first ultrasound volume data and the contrast enhanced volume data. When the position aligning process is performed by using a position sensor, the initial position aligning process based on a structure rendered in the surrounding of the region of interest does not necessarily have to be performed.

The position aligning process may be performed not only by using a structure such as a blood vessel but also by applying a publicly-known technique such as a mutual information value or an image correlation to pieces of contrast enhanced volume data that are in substantially the same temporal phase before and after the treatment or to pieces of tissue volume data before and after the treatment. In that situation, for example, after having acquired the first ultrasound volume data, the 2doctor acquires pre-RFA-treatment contrast enhanced volume data in the same three-dimensional scanning region as that of the first ultrasound volume data. The pre-RFA-treatment contrast enhanced volume data is, for example, contrast enhanced volume data of an arterial phase in which the blood vessel structure is imaged with a dye. After that, the obtaining unit 17 obtains a piece of contrast enhanced volume data that is in the same temporal phase as that of the pre-RFA-treatment contrast enhanced volume data, from a group of contrast enhanced volume data acquired when the puncture needle 5 has been pulled out after the RFA treatment. Subsequently, the obtaining unit 17 performs a position aligning process between these two pieces of contrast enhanced volume data by implementing a method that uses a mutual information value, an image correlation, or the like. As a result, the obtaining unit 17 is able to accurately perform the position aligning process between the first ultrasound volume data and the contrast enhanced volume data.

Alternatively, for example, the doctor may acquire tissue volume data using a B-mode before acquiring post-RFA-treatment contrast enhanced volume data. Subsequently, the obtaining unit 17 performs a position aligning process between the first ultrasound volume data and the tissue volume data by implementing a method that uses a mutual information value, an image correlation, or the like. As a result, the obtaining unit 17 is able to accurately perform the position aligning process between the first ultrasound volume data and the contrast enhanced volume data. When implementing a method that uses a mutual information value, an image correlation, or the like, it is also acceptable to further perform the position aligning process described above that employs the position sensor.

After that, based on the result of the position aligning process, the obtaining unit 17 obtains the position of a boundary MA' of the corresponding region in the volume space of the contrast enhanced volume data, as illustrated in the left section of FIG. 15B. In this situation, the obtaining unit 17 associates the volume space of the first ultrasound volume data with the real space when the region of interest was set, or the like. In addition, the obtaining unit 17 has already completed associating the volume space of the contrast enhanced volume data with the volume space of the first ultrasound volume data, by performing the position aligning process. Accordingly, as illustrated in the right section of FIG. 15B, the obtaining unit 17 is able to obtain the position of a boundary MA of the corresponding region in the real space, based on the boundary MA' of the corresponding region in the volume space of the contrast enhanced volume data.

After that, the image generating unit 14 according to the third embodiment generates second ultrasound image data (second ultrasound volume data) based on the position of the boundary of the corresponding region.

Subsequently, in the third embodiment also, the display-purpose image data, the temporal change curve, and the ratio described in the first embodiment are displayed. Except for the configuration in which the position of the boundary of the region corresponding to the region of interest in the contrast enhanced volume data is obtained by performing the position aligning process, the explanations of the first and the second embodiments are also applied to the third embodiment. Further, the processes performed by the ultrasound diagnostic apparatus according to the third embodiment are the same as those in the first embodiment, except that the process at step S102 in FIG. 11 is performed by using the boundary of the corresponding region. Thus, the explanation will be omitted.

In the third embodiment, even if the effect of the treatment is judged after the puncture needle 5 has been pulled out, it is possible to accurately obtain the position of the corresponding region in the contrast enhanced volume data based on the result of the position aligning process, because the position of the region of interest is accurately obtained. Further, because the position aligning process in the third embodiment is a position aligning process performed between the pieces of ultrasound volume data, it is possible to perform the position aligning process more accurately and more promptly than a position aligning process performed between pieces of other types of volume data. Accordingly, in the third embodiment, it is possible to promptly and conveniently judge the effect of the radiofrequency ablation treatment, without fail, during an arbitrary time period.

Fourth Embodiment

Figure 16:
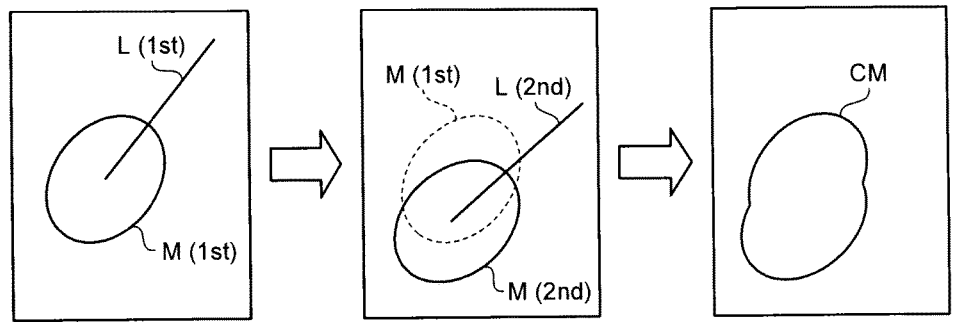
FIG. 16 is a drawing for explaining a fourth embodiment.

In a fourth embodiment, a modification example that is applied to a situation where a treatment using the puncture needle 5 is performed multiple times while changing the position of the puncture needle 5 will be explained, with reference to FIG. 16 and so on. FIG. 16 is a drawing for explaining the fourth embodiment.

During an RFA treatment, the ablation process is usually performed multiple times while changing the position of the puncture needle 5. In the first and the second embodiments described above, if it is determined at step S6 that the position of the puncture needle 5 needs to be changed, the processes at steps S1 through S4 are performed again. In that situation, after the position of the puncture needle 5 is changed, a new region of interest is set at step S2. After that, by using the boundary of the new region of interest, image data used for judging the effect of the treatment is generated and displayed.

For the doctor, however, it is desirable to judge the effect of the treatment by combining the currently-set region of interest with one or more regions of interest set in the past.

For this reason, when a treatment using the puncture needle 5 is performed multiple times while changing the position of the puncture needle 5, the obtaining unit 17 according to the fourth embodiment obtains the position of the boundary of a combined region obtained by combining a plurality of regions of interest that are set in the each treatment. After that, based on the position of the boundary of the combined region, the image generating unit 14 according to the forth embodiment generates second ultrasound image data.

In the left section of FIG. 16, "L(1st)" indicates an insertion path in the real space through which the puncture needle 5 was inserted during an ablation treatment for the first time. In the left section of FIG. 16, "M(1st)" indicates the real-space position of the boundary of the region of interest that is set based on the position of "the tip (the needle tip of the puncture needle 5) of the insertion path L(1st)". In the middle section of FIG. 16, "L(2nd)" indicates an insertion path in the real space through which the puncture needle 5 was inserted during an ablation treatment for the second time, to change the ablating position because the ablation treatment performed the first time was insufficient. In the middle section of FIG. 16, "M(2nd)" indicates the real-space position of the boundary of the region of interest that is set based on the position of "the tip (the needle tip of the puncture needle 5) of the insertion path L(2nd)".

In that situation, as illustrated in the right section of FIG. 16, the obtaining unit 17 obtains the position of a combined boundary CM obtained by combining the boundary M(1st) with the boundary M(2nd). Further, the obtaining unit 17 also obtains the position of a combined boundary in the volume space that corresponds to the combined boundary CM in the real space.

After that, the obtaining unit 17 exercises control so that the image generating unit 14 generates second ultrasound image data (second ultrasound volume data) by using one threshold value (or a plurality of threshold values) and the setting information. Subsequently, the image generating unit 14 generates various types of display-purpose image data explained in the first embodiment, by using the second ultrasound volume data and outputs the display-purpose image data to the monitor 2. For example, the monitor 2 displays image data in which lines indicating the positions of the boundary M(1st) and the boundary M(2nd) are superimposed on MPR image data generated from the second ultrasound volume data based on the combined boundary.

As explained above, according to the fourth embodiment, by generating and displaying the second ultrasound image data that uses the combined boundary, it is possible to comprehensively, promptly, and conveniently judge the effect of the radiofrequency ablation treatment performed multiple times. As a modification example of the fourth embodiment, for example, the controlling unit 19 may cause the second ultrasound image data to be generated and displayed based on the position of the boundary of the newest region of interest, so that, when the second ultrasound image data is generated and displayed, the boundaries of the last and the second from the last regions of interest are displayed with dotted lines.

Fifth Embodiment

Figure 17:
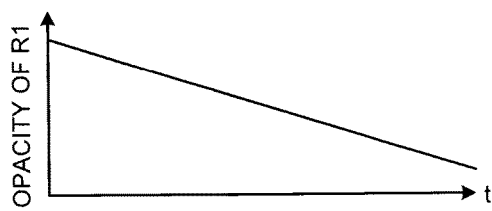
FIG. 17 and FIG. 18 are drawings for explaining a fifth embodiment.
Figure 18:
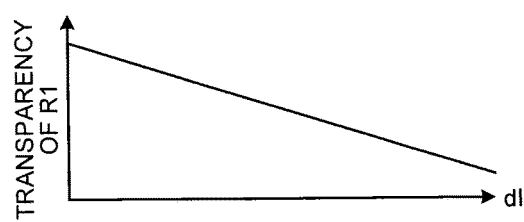

In a fifth embodiment, modifications examples of the setting information that are applicable to any of the first to the fourth embodiments will be explained, with reference to FIGS. 17, 18 and so on. FIGS. 17 and 18 are drawings for explaining the fifth embodiment.

In the first to the fourth embodiments described above, the second ultrasound image data (the second ultrasound volume data) is generated by assigning a pixel value (e.g., a color) to each of pixels of which the change of the brightness value between before and after the contrast enhancement is equal to or larger than the threshold value, the assigned pixel value corresponding to the distance between the pixel and the boundary of the region of interest. By viewing the second ultrasound image data, the doctor is able to judge whether any bloodstream remains on the inside or the outside of the region of interest. In this situation, it is also important for the doctor who judges the effect of the treatment, to judge whether the bloodstream remaining after the ablation treatment is a bloodstream flowing through a blood vessel (e.g., through a tumor-feeding blood vessel) or a perfusion flowing through a tissue by capillaries.

During a contrast enhanced imaging process, the contrast agent flows into capillaries after flowing into blood vessels. In other words, during a contrast enhanced imaging process, the brightness values increase on the inside of the capillaries, after the brightness values increase on the inside of the blood vessels. For this reason, the image generating unit 14 according to the fifth embodiment generates second ultrasound image data by assigning a pixel value to each of pixels of which the change of the brightness value between before and after the contrast enhancement is equal to or larger than the threshold value, the assigned pixel value corresponding to the distance between the pixel and the boundary of the region of interest and to the time at which the change of the brightness value of the pixel became equal to or larger than the threshold value. For example, the internal storage unit 18 stores setting information in which mutually-different pixel values are set depending on mutually-different distances from the boundary and mutually-different times. In one example, the internal storage unit 18 stores color information in which mutually-different colors are set depending on the mutually-different distances from the boundary and the mutually-different times. In other words, the color information described here is color information obtained by adding an axis expressing time, to the color information illustrated in FIG. 6A or FIG. 14.

For example, as illustrated in FIG. 17, the internal storage unit 18 stores color information in which the opacity of the tone "R1" decreases as the time (t) elapses. The obtaining unit 17 causes the image generating unit 14 to generate second ultrasound image data (second ultrasound volume data) by using the color information illustrated in FIG. 17. In the second ultrasound image data generated from this process, the pixels are rendered in a manner that the earlier the location of a pixel exceeded the threshold value, the higher is the level of opacity of the color in which the pixel is rendered and in a manner that the later the location a pixel exceeded the threshold value, the higher is the level of transparency of the color in which the pixel is rendered. Accordingly, the doctor is able to distinguish the bloodstream from the perfusion by understanding the levels of transparency, even if the same tone is used.

Further, in contrast enhanced imaging, the degree by which the brightness values increase is higher on the inside of blood vessels, whereas the degree by which the brightness values increase is lower on the inside of capillaries. For this reason, the image generating unit 14 according to the fifth embodiment generates second ultrasound image data by assigning a pixel value to each of pixels of which the change of the brightness value between before and after the contrast enhancement is equal to or larger than the threshold value, the assigned pixel value corresponding to the distance between the pixel and the boundary of the region of interest and to the amount of the change of the brightness value of the pixel. For example, the internal storage unit 18 stores setting information in which mutually-different pixel values are set depending on mutually-different distances from the boundary and mutually-different times. In one example, the internal storage unit 18 stores color information in which mutually-different colors are set depending on mutually-different distances from the boundary and mutually-different amounts of change (dI=I-I0) of the brightness value. In other words, the color information described here is color information obtained by adding an axis expressing the amounts of change, to the color information illustrated in FIG. 6A or FIG. 14.

For example, as illustrated in FIG. 18, the internal storage unit 18 stores color information in which the level of transparency of the tone "R1" decreases, as the amount of change (dI) in the brightness value increases. The obtaining unit 17 causes the image generating unit 14 to generate second ultrasound image data (second ultrasound volume data) by using the color information illustrated in FIG. 17. In the second ultrasound image data generated from this process, the pixels are rendered in a manner that the larger the "dI" value of the location of a pixel is, the higher is the level of opacity of the color in which the pixel is rendered and in a manner that the smaller the "dI" value of the location of a pixel is, the higher is the level of transparency of the color in which the pixel is rendered. Accordingly, the doctor is able to distinguish the bloodstream from the perfusion by understanding the levels of transparency, even if the same tone is used.

Further, besides the arrangement in which the levels of transparency of the colors are varied, the fifth embodiment is also applicable to a situation where, for example, the levels of shades of the colors are varied with respect to the added axis. Further, the fifth embodiment is also applicable to a situation where the hatching information or the shade-level information is used, besides the color information.

As explained above, according to the fifth embodiment, it is possible to generate and display the map image data that makes it possible to distinguish whether the bloodstream remaining after the ablation treatment is, for example, a bloodstream on the inside of a tumor-feeding blood vessel or a perfusion.

In the first to the fifth embodiments described above, the example is explained in which the image process is performed on the volume data generated by the three-dimensional scan. However, the image process explained in any of the first to the fifth embodiments is applicable to two-dimensional image data generated by a two-dimensional scan.

The constituent elements of the apparatuses that are illustrated in the drawings are based on functional concepts. Thus, it is not necessary to physically configure the elements as indicated in the drawings. In other words, the specific mode of distribution and integration of the apparatuses is not limited to the ones illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a computer program that is analyzed and executed by the CPU or may be realized as hardware using wired logic.

Furthermore, the image processing methods explained in the first to the fifth embodiments may be realized by causing a computer such as a personal computer or a workstation to execute an image processing computer program (hereinafter, an "image processing program") that is prepared in advance. The image processing program may be distributed via a network such as the Internet. Further, it is also possible to record the image processing program onto a computer-readable non-transitory recording medium such as a hard disk, a flexible disk (FD), a Compact Disk Read-Only Memory (CD-ROM), a Magneto-optical (MO) disk, or a Digital Versatile Disk (DVD), so that a computer is able to read the image processing program from the recording medium and to execute the read image processing program.

As explained above, according to at least one of the embodiments, it is possible to promptly and conveniently judge the effect of the radiofrequency ablation treatment, without fail.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising:
processing circuitry configured to
obtain a position of a boundary of a region of interest that is set in first ultrasound image data of a subject,
generate second ultrasound image data by assigning a pixel value to each of pixels of which a change of a brightness value between before and after a contrast enhancement is equal to or larger than a threshold value with regard to pre-contrast-enhanced image data and post-contrast-enhanced image data of the subject both of which were acquired after a treatment using a puncture needle has been performed, the assigned pixel value corresponding to a distance between the pixel and the boundary of the region of interest, and
cause a display to display the second ultrasound image data.

2. The ultrasound diagnostic apparatus according to claim 1, further comprising: memory circuitry configured to store therein the threshold value for the change of the brightness value and setting information in which mutually-different pixel values are set depending on distances from the boundary, wherein
the processing circuitry is configured to generate the second ultrasound image data based on the setting information.

3. The ultrasound diagnostic apparatus according to claim 2, wherein the memory circuitry is configured to store therein, as the setting information, color information in which mutually-different colors are set, or hatching information in which mutually-different hatchings are set, or shade-level information in which mutually-different levels of shade of similar colors are set, depending on distances from the boundary.

4. The ultrasound diagnostic apparatus according to claim 3, wherein the processing circuitry is further configured to
detect a position of a needle tip of the puncture needle by employing a position sensor with which the puncture needle is provided, and
obtain the position of the boundary of the region of interest based on the position of the needle tip.

5. The ultrasound diagnostic apparatus according to claim 4, wherein
the first ultrasound image data is first ultrasound volume data generated by three-dimensionally scanning the subject, whereas
contrast enhanced image data represented by the pre-contrast-enhanced image data and the post-contrast-enhanced image data is contrast enhanced volume data generated by three-dimensionally scanning the subject,
the processing circuitry is configured to
obtain a three-dimensional position of the region of interest based on a three-dimensional position of the needle tip,
generate, as the second ultrasound image data, second ultrasound volume data by assigning a voxel value to each of voxels of which a change of a brightness value between before and after the contrast enhancement is equal to or larger than the threshold value with regard to the contrast enhanced volume data represented by the pre-contrast-enhanced image data and the post-contrast-enhanced image data, the assigned voxel value corresponding to a distance between the voxel and the boundary of the region of interest based on the setting information, and
cause the display to display one or both of cross-sectional image data and projection image data that are generated from the second ultrasound volume data.

6. The ultrasound diagnostic apparatus according to claim 1, wherein the processing circuitry is configured to cause the display to display image data obtained by superimposing together the second ultrasound image data with at least one selected from the following: ultrasound image data rendering a tissue of the subject; and ultrasound image data rendering a contrast agent distribution in the subject.

7. The ultrasound diagnostic apparatus according to claim 3, wherein the memory circuitry is configured to store therein, as the setting information, color information in which mutually-different colors in a first tone are set on an inside of the boundary depending on mutually-different distances from the boundary, whereas mutually-different colors in a second tone that is different from the first tone are set on an outside of the boundary depending on mutually-different distances from the boundary.

8. The ultrasound diagnostic apparatus according to claim 1, wherein the processing circuitry is configured to generate the second ultrasound image data for an inside of the region of interest, or the inside of the region of interest and a region that is limited to a region positioned near the boundary.

9. The ultrasound diagnostic apparatus according to claim 3, wherein
the memory circuitry is configured to store therein a plurality of threshold values that are mutually different depending on the mutually-different distances from the boundary, as the threshold value for the change of the brightness value, and the processing circuitry is configured to generate the second ultrasound image data by assigning a pixel value to each of pixels of which a value is equal to or larger than the threshold value corresponding to the distance from the boundary of the region of interest, the assigned pixel value corresponding to the distance between the pixel and the boundary of the region of interest, based on the setting information.

10. The ultrasound diagnostic apparatus according to claim 1, wherein the processing circuitry is configured to cause the second ultrasound image data to be displayed while being limited to the region of interest or causes the position of the puncture needle to be displayed while being superimposed on the second ultrasound image data limited to the region of interest.

11. The ultrasound diagnostic apparatus according to claim 5, wherein the processing circuitry is configured to cause cross-sectional image data to be displayed, the cross-sectional image data being obtained by cutting off the second ultrasound volume data on a cross-sectional plane in the second ultrasound volume data that contains the needle tip of the puncture needle and that is orthogonal to an insertion path of the puncture needle.

12. The ultrasound diagnostic apparatus according to claim 1, wherein the processing circuitry is further configured to cause a temporal change curve to be displayed so as to indicate time dependence of the brightness value in the region of interest.

13. The ultrasound diagnostic apparatus according to claim 1, wherein the processing circuitry is further configured to cause a ratio to be displayed, the ratio being a ratio of a region to which the pixel values have been assigned within the region of interest, to the region of interest.

14. The ultrasound diagnostic apparatus according to claim 1, wherein
when contrast enhanced image data represented by the pre-contrast-enhanced image data and the post-contrast-enhanced image data is acquired after the puncture needle has been pulled out, the processing circuitry is configured to
perform a position aligning process on the first ultrasound image data and the contrast enhanced image data and obtains a position of a corresponding region in the contrast enhanced image data that corresponds to the region of interest, and
generate the second ultrasound image data based on a position of a boundary of the corresponding region.

15. The ultrasound diagnostic apparatus according to claim 1, wherein
when a treatment using the puncture needle is performed multiple times while changing a position of the puncture needle, the processing circuitry is configured to
obtain a position of a boundary of a combined region obtained by combining a plurality of regions of interest that are set in the multiple treatments, and
generate the second ultrasound image data based on the position of the boundary of the combined region.

16. The ultrasound diagnostic apparatus according to claim 1, wherein the processing circuitry is configured to generate the second ultrasound image data by assigning a pixel value to each of pixels of which the change of the brightness value between before and after the contrast enhancement is equal to or larger than the threshold value, the assigned pixel value corresponding to the distance between the pixel and the boundary of the region of interest and to a time at which the change of the brightness value of the pixel is equal to or larger than the threshold value.

17. The ultrasound diagnostic apparatus according to claim 1, wherein the processing circuitry is configured to generate the second ultrasound image data by assigning a pixel value to each of pixels of which the change of the brightness value between before and after the contrast enhancement is equal to or larger than the threshold value, the assigned pixel value corresponding to the distance between the pixel and the boundary of the region of interest and to an amount of the change of the brightness value of the pixel.

18. The ultrasound diagnostic apparatus according to claim 1, wherein a shape template of the region of interest is determined in accordance with a type of the puncture needle.

19. An image processing method comprising:
a process performed by processing circuitry to obtain a position of a boundary of a region of interest that is set in first ultrasound image data of a subject;
a process performed by the processing circuitry to generate second ultrasound image data by assigning a pixel value to each of such pixels of which a change of a brightness value between before and after a contrast enhancement is equal to or larger than a threshold value with regard to pre-contrast-enhanced image data and post-contrast-enhanced image data of the subject both of which were acquired after a treatment using a puncture needle has been performed, the assigned pixel value corresponding to a distance between the pixel and the boundary of the region of interest; and
a process performed by the processing circuitry to cause a display unit to display the second ultrasound image data.

* * * * *